(12) United States Patent
Iversen

(10) Patent No.: US 6,673,778 B1
(45) Date of Patent: *Jan. 6, 2004

(54) ENZYME INHIBITORS FOR METABOLIC REDIRECTION

(75) Inventor: Patrick L. Iversen, Corvallis, OR (US)

(73) Assignee: The Board of Regents of the University of Nebraska, Lincoln, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/737,452

(22) Filed: Dec. 13, 2000

Related U.S. Application Data

(63) Continuation-in-part of application No. 09/574,570, filed on May 17, 2000, which is a continuation-in-part of application No. 08/802,859, filed on Feb. 19, 1997, now abandoned.
(60) Provisional application No. 60/012,219, filed on Feb. 23, 1996.

(51) Int. Cl.$^7$ .................. A61K 31/70; C07H 21/04; C12N 5/00
(52) U.S. Cl. .................. 514/44; 536/23.1; 536/24.3; 536/24.31; 536/24.33; 536/24.5; 435/6; 435/325; 435/375
(58) Field of Search .................. 536/23.1, 24.3, 536/24.31, 24.33, 24.5; 435/6, 325, 375, 455; 514/44

(56) References Cited

U.S. PATENT DOCUMENTS 5,585,479 A 12/1996 Hoke et al.

FOREIGN PATENT DOCUMENTS

WO  WO 00/20432 A1  4/2000
WO  WO 00/24885 A2  5/2000

OTHER PUBLICATIONS

Chirila et al. Biomaterials vol. 23, pp. 321–342, 2002.*
Ingelman–Sundberg, Journal of Internal Medicine, vol. 250, pp. 186–200, 2001.*
Andrea D. Branch, A good antisense molecule is hard to find, TIBS, 47–48, 1998.*
Stanley T. Crooke, Basic Principles of Antisense Therapeutics, Springer–Verlag, NY, p. 3., 1998.*
Stein et al. Pharmacology & Therapeutics (2000), vol. 85, pp. 231–236.*
All references have been previously forwarded to Applicants in parent application 09/574,570.*
Branch, A.D., "A good antisense molecule is hard to find" *TIBS* 23:45–50 (1998).
Bristow, J., et al., "Antisense RNA regulation by transcripts from the human F450c21 B gene and P450c21A "pseudogene"" *Clinical Research* 41(2):272A abstract only (1993).
Cai, Y., et al., "Inhibition of metabolism of benzo[a]pyrene by a c–5 propyne antisense oligonucletide against cytochrome P450 1A1 in mouse hepatoma cell line (Hepa–1)" *SOT Annual Meeting* pp. 21 abstract # 101 (1998).

Correia, M.A. and Castagnoli, Jr., N., "Pharmacokinetics: Drug Biotransformation" *Basic and Clinical Pharmacology* Katzung (ed.) Appleton & Lange, Los Altos, CA, pp. 36–37 (1987).
DeLong, R.K., et al., "Comparative Pharmacokinetics, Tissue Distribution, and Tumor Accumulation of Phosphorothioate, Phosphorodithioate, and Methylphosphonate Oligonucleotides in Nude Mice" *Antisense & Nucleic Acid Drug Development* 7:71–77 (1997).
Desjardins, J.P. and Iversen, P.L., "Inhibition of the Rat Cytochrome P450 3A2 by an Antisense Phosphorothioate Oligodeoxynucleotide In Vivo" *J. of Pharmacology and Experimental Therapeutics* 275(3):1608–1613 (1995).
Desjardins, J., et al., "Cholesteryl–Conjugated Phosphorothioate Oligodeoxynucleotides Modulate CYP2B1 Expression In Vivo" *J. of Drug Targeting* 2:477–485 (1995).
Einolf, H.J. and Baird, W.M., "Effects of antisense oligonucleotides on the metabolism of benzo(a)pyrene by P4501A1 in the mouse hepatoma cell line, Hepa–1" *Proceedings of the American Association for Cancer Research Annual Meeting* 35:134 abstract # 801 (1994).
Gewirtz, A.M., et al., "Facilitating oligonucleotide delivery: Helping antisense deliver on its promise" *Proc Natl Acad Sci USA* 93:3161–3163 (1996).
Hanecak, R., et al., "Antisense Oligonucleotide Inhibition of Hepatitis C Virus Gene Expression in Transformed Hepatocytes" *Journal of Virology* 70(8):5203–5212 (1996).
Hangeland, J.J., et al., "Tissue Distribution and Metabolism of the [$^{32}$P]–Labeled Oligodeoxynucleoside Methylphosphonate–Neoglycopeptide Conjugate, [YEE(ah–GalNAc)$_3$] –SMCC–AET–pU$^m$pT7, in the Mouse" *Antisense & Nucleic Acid Drug Development* 7:141–149 (1997).
Nelson, D.R., et al., "The P450 Superfamily: Update on New Sequences, Gene Mapping, Accession Numbers, Early Trivial Names of Enzymes, and Nomenclature" *DNA and Cell Biology* 12(1):1–51 (1993).
Rojanasakul, Y., "Antisense oligonucleotide therapeutics: drug delivery and targeting" *Advanced Drug Delivery Reviews* 18:115–131 (1996).
Sindhu, R.K., et al., "Inhibition of Cytochrome P450 1A1 by Antisense Phosphorothioate Oligonucleotide in Hepa Ic1c7 Cells" *Biochemical and Biophysical Research Communications* 229:673–680 (1996).

* cited by examiner

Primary Examiner—Sean McGarry
Assistant Examiner—Janet L. Epps-Ford
(74) Attorney, Agent, or Firm—Heidi S. Nebel; Lee Ann Gorthey; Perkins Coie LLP

(57) ABSTRACT

A method is described for improving the pharmacokinetics of a drug in a subject, by co-administering oligomers, preferably PMO's (phosphorodiamidate morpholino oligonucleotides), antisense to RNAs encoding drug-metabolizing enzymes, particularly p450 enzymes. The oligomers reduce production of the drug-metabolizing enzymes, which extends drug half-life and effectiveness and/or decreases drug toxicity.

15 Claims, 7 Drawing Sheets

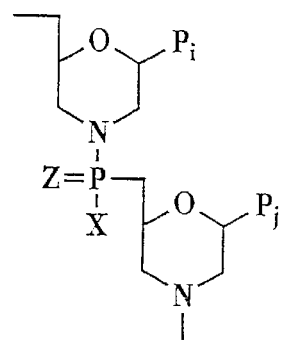
Fig. 6A-A
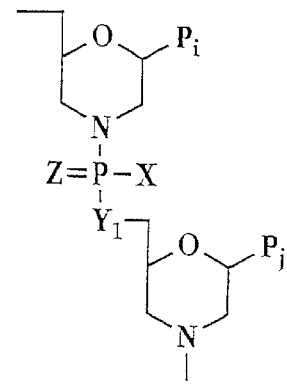
Fig. 6B-B
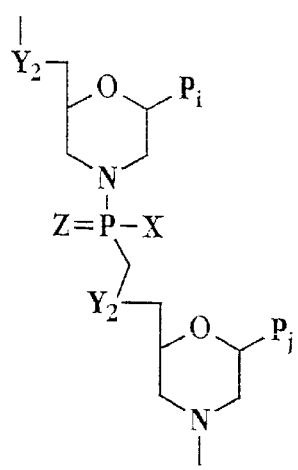
Fig. 6C-C
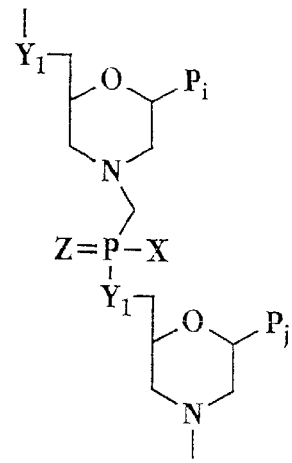
Fig. 6D-D/E-E

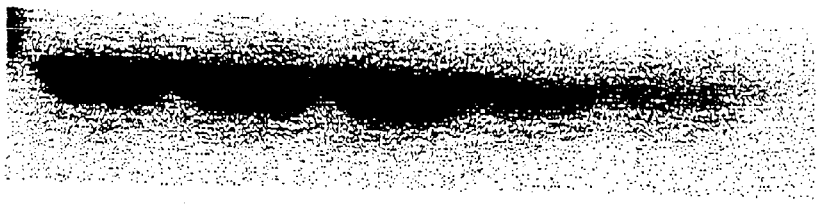
Fig. 7

ENZYME INHIBITORS FOR METABOLIC REDIRECTION

CROSS-REFERENCE TO RELATED APPLICATIONS

This application is a continuation-in-part of application Ser. No. 09/574,570, filed May 17, 2000 which is a continuation-in-part of application Ser. No. 08/802,859, filed Feb. 19, 1997 now abandoned, which is a continuation of provisional application Ser. No. 60/012,219, filed Feb. 23, 1996, each of which is hereby incorporated by reference in its entirety.

FIELD OF THE INVENTION

The present invention relates to methods of improving the performance of drugs which are metabolized by p450 enzymes, by antisense inhibition of the particular enzyme. Typically, the p450 enzyme is induced by an exogenous substance or by the drug itself.

BACKGROUND OF THE INVENTION

When a drug is introduced to a biological system, multiple pharmacokinetic processes begin to affect the ultimate efficiency of the drug, determining how rapidly, in what concentration, and for how long the drug will be available to the target organ. In general, lipophilic xenobiotics are metabolized to more polar and hence more readily excretable products. The role metabolism plays in the inactivation of lipid soluble drugs can be quite dramatic. For example, lipophilic barbiturates such as thiopental and phenobarbital would have extremely long half-lives were it not for their metabolic conversion to more water soluble compounds. Many potential anticancer drugs are deemed unbeneficial because their half-life is too brief to achieve any useful therapeutic effect.

The metabolic conversion of an ingested compound (such as a drug or a food additive) into a form which is readily cleared from the body is termed biotransformation or detoxification. Compounds ingested by organisms are generally biotransformed in two phases.

In Phase 1, termed functionalization, a reactive site, such as an amine, thiol, or hydroxyl group, is introduced, generally via an oxidation reaction. In Phase 2, termed conjugation, a water-soluble group is added to the reactive site. Phase 2 typically involves addition of a glucuronic acid, sulfuric acid, acetic acid or amino acid to the compound.

Phase 1 reactions are frequently catalyzed by the cytochrome p450 superfamily of enzymes. In a typical Phase 1 reaction, a cytochrome p450 enzyme uses oxygen and NADH to add a reactive group, such as a hydroxyl radical, to a drug. The reactive intermediates produced may be much more toxic than the parent molecule, and may cause damage to proteins, RNA, and DNA within the cell (Vermeulen, N.P.E., "Role of metabolism in chemical toxicity," in: Ioannides, C., ed., CYTOCHROME P450: METABOLIC AND TOXICOLOGICAL ASPECTS. Boca Raton, Fla.: CRC Press, Inc; 1996, pp 29–53).

Phase 2 conjugation reactions, which generally follow Phase 1 activation reactions, often reduce the toxicity of reactive intermediates formed by Phase 1 reactions. Phase 2 conjugation transforms the drug into a water-soluble compound that can be excreted, e.g. through urine or bile. Several types of conjugation reactions occur in the body, including glucuronidation, sulfation, and glutathione and amino acid conjugation. In some instances, the parent drug may already possess a functional group that forms a conjugate directly. For example, the hydrazide moiety of isoniazide is known to form an acetyl conjugate in a Phase 2 reaction. This conjugate is then a substrate for a Phase 1 type reaction, namely, hydrolysis to isonicotinic acid. Thus, Phase 2 reactions may in some instances actually precede Phase 1 reactions.

Correlations have been noted between altered Phase 1 and/or Phase 2 metabolic activities and increased risk of diseases such as cancers and liver disease, and in adverse drug responses. For example, some drugs (such as acetaminophen) are metabolically converted to reactive intermediates that are toxic to various organs. These toxic reactions may not be apparent at low drug dosages, when subsequent steps or alternative pathways are not overwhelmed or compromised and the availability of endogenous co-substrates (glutathione, glucuronic acid, sulfate) is not limited. When these resources are exhausted, however, the toxic pathway may prevail, resulting in overt organ toxicity or carcinogenesis.

Many drugs and other xenobiotic agents are capable of inducing genes which encode drug-metabolic enzymes, enhancing the levels of these enzymes and, consequently, accelerating the metabolic reactions catalyzed by these enzymes. Such accelerated metabolism may cause a decrease in the half-life and pharmacologic efficacy of the substrate drug. Induction genes encoding drug-metabolizing compounds could exacerbate drug-mediated tissue toxicity by increasing steady-state levels of reactive or toxic intermediates.

A need exists in the art for modulating the pharmacokinetics of various drugs in patients. The present invention achieves this by decreasing the production of one or more specific drug-metabolizing enzymes which are induced either by the drug itself or by another xenobiotic agent to which the patients have been exposed. Decreased drug metabolism results in an increased drug half-life. The dosage of the drug can then be reduced, since the lower dose has equivalent bioavailability to that of a higher dose in the absence of such modulation, and toxicities associated with high drug dosage can be circumvented. Reducing the availability of metabolically toxic pathways thus increases the safety of the drug.

SUMMARY OF THE INVENTION

In one aspect, the invention provides a method of improving the pharmacokinetics of a drug administered to a subject, where the drug is known to be metabolized in vivo by a cytochrome p450 enzyme that reduces the effectiveness of the drug. In accordance with the method, one co-administers with the drug a morpholino antisense oligomer effective to reduce synthesis of the drug-metabolizing cytochrome p450 enzyme, by hybridizing to a target RNA molecule which encodes the enzyme. In preferred embodiments of the method, the drug itself induces the drug-metabolizing p450 enzyme, or the subject has been exposed to a xenobiotic agent which induces such an enzyme.

In one embodiment, the antisense oligomer hybridizes to a region of the target RNA molecule which includes the AUG translation start site. In another embodiment, the target RNA molecule is pre-mRNA, and the antisense oligomer hybridizes to a region of the pre-mRNA which includes an intron-exon boundary or an exon-intron boundary.

Preferably, the antisense oligomer is at least 15 nucleotides in length. Preferred oligomers are morpholino oligomers having an uncharged backbone comprising phosphoramidate or, preferably, phosphorodiamidate linkages. The antisense oligomer preferably hybridizes to a region of the target RNA with a $T_m$ greater than 37° C. The sequence of the oligonucleotide can be one selected from the group consisting of SEQ ID NOs: 16–35 and 46–47, preferably from SEQ ID NOs: 26–35 and 46–47 (targeted to human RNA sequences), and more preferably from SEQ ID NOs: 27, 30, 34, 35, and 46–47.

The targeted cytochrome p450 enzyme is preferably selected from the group consisting of CYP1A1, CYP1A2, CYP2A6, CYP2B1, CYP2C9, CYP2C19, CYP2D6, CYP2E1, CYP3A2, CYP3A4, and CYP6A1 enzymes. In a preferred embodiment, where the subject is a human subject, the cytochrome p450 is preferably selected from the group consisting of CYP1A1, CYP1A2, CYP2A6, CYP2B1, CYP2C9, CYP2C19, CYP2D6, CYP2E1, and CYP3A4 enzymes, and more preferably from the group consisting of CYP1A2, CYP2B1, CYP2E1, and CYP3A4 enzymes.

In selected embodiments, the enzyme is CYP2E1, and the drug is acetaminophen, or the enzyme is from the CYP2B or CYP3A subfamily, preferably CYP2B1, and the drug is phenobarbital or hexobarbital. In further embodiments, the enzyme is CYP3A4, and the drug is an antibiotic selected from the group consisting of clarithromycin, erythromycin, rifampicin, rifampin, rifabutin, and rapamycin; or the enzyme is CYP3A4 or CYP1A2, and the drug contains an estrogen or estradiol. In still further embodiments, the enzyme is CYP3A4, the drug is a protease inhibitor or a non-nucleoside reverse transcriptase inhibitor, and the inducing xenobiotic is a CYP3A4-inducing non-nucleoside reverse transcriptase inhibitor.

In a preferred embodiment, the antisense oligomer is administered orally to the subject, typically in an amount of at least 1 mg/kg body weight. In another preferred embodiment, the oligomer is administered transdermally.

These and other objects and features of the invention will become more fully apparent when the following detailed description of the invention is read in conjunction with the accompanying drawings.

BRIEF DESCRIPTION OF THE DRAWINGS

FIGS. 6A—A to 6E—E show the repeating subunit segment of exemplary morpholino oligonucleotides, designated A—A through E—E, constructed using subunits A–E, respectively, of FIG. 5; and FIG. 7 shows a Western blot of liver microsome samples comparing relative levels of CYP3A2 isozyme in rats injected i.p. with saline (lane 1), or with 15 nmoles of CYP3A2 antisense PMO, SEQ ID NO: 25 (lanes 2 and 3), or orally administered 60 nmoles of CYP3A2 antisense PMO (lanes 4 and 5), 24 hours prior to organ harvesting, where the lanes labeled "NADPH Reductase" are a control for total protein on the blot.

DETAILED DESCRIPTION OF THE INVENTION

I. Definitions

Figure 1:
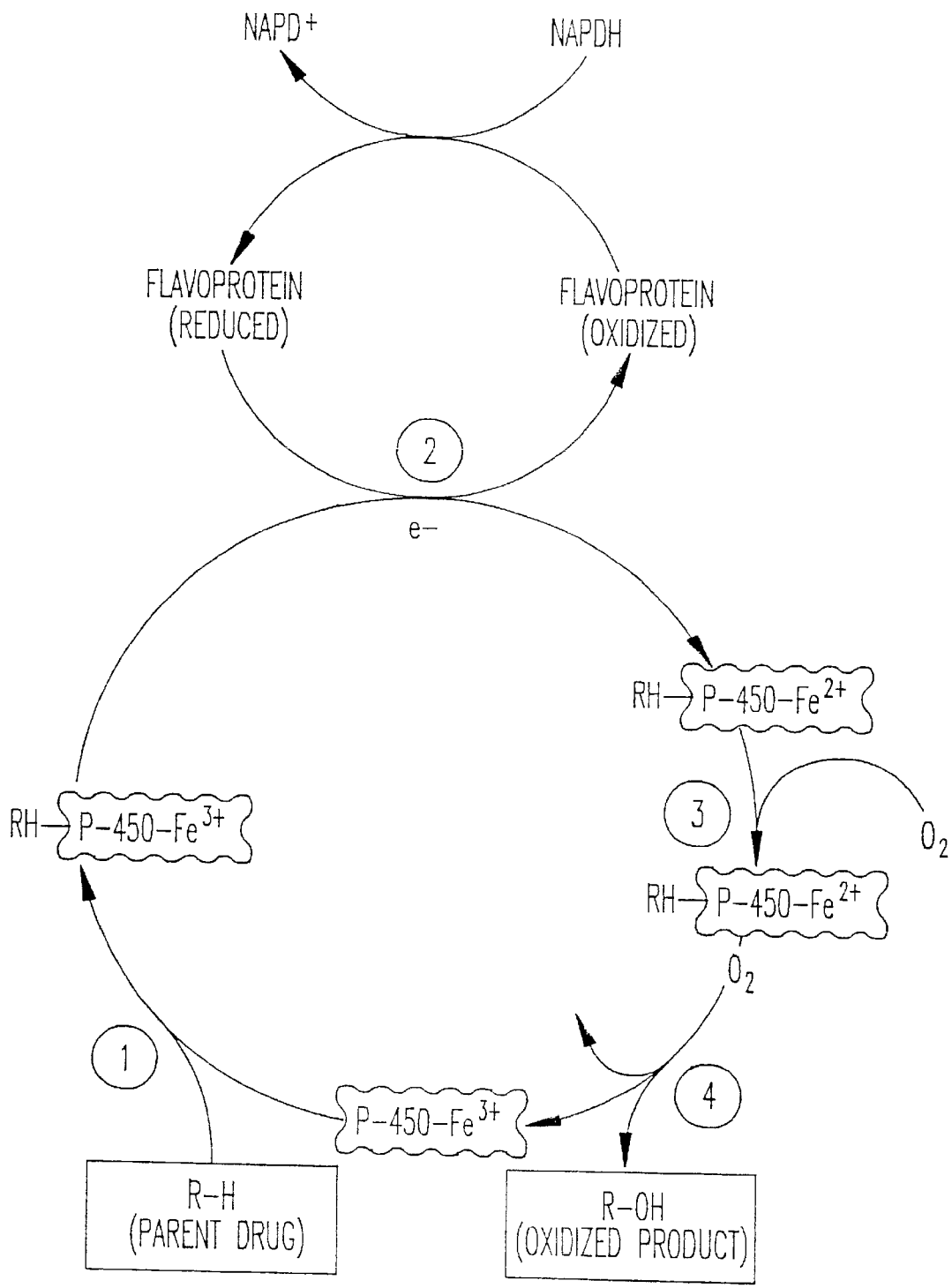
FIG. 1 shows the steps in oxidation of a drug by a cytochrome p450.

The terms below, as used herein, have the following meanings, unless indicated otherwise:

A "xenobiotic" is a chemical substance which is foreign to a biological system. Xenobiotics include: naturally occurring compounds which are foreign, i.e., non-native, to the biological system in question, drugs, environmental agents, carcinogens, and insecticides.

A "drug" refers to a chemical substance administered to an animal for a therapeutic purpose. Such agents may take the form of ions, small organic molecules, peptides, proteins or polypeptides, oligonucleotides, and oligosaccharides, for example. The agent is typically administered to cause an observable and desirable change in the structure, function, or composition of a cell upon uptake by the cell. Such changes include, for example, increased or decreased expression of one or more mRNAs, increased or decreased expression of one or more proteins, phosphorylation of a protein or other cell component, inhibition or activation of an enzyme, inhibition or activation of binding between members of a binding pair, an increased or decreased rate of synthesis of a metabolite, or increased or decreased cell proliferation.

"Induction" of a gene refers to the switching on or enhancement of expression of the gene by a stimulus such as an inducer molecule, e.g. a hormone or exogenous substance, or by another stimulus such as heat. In the context of the present invention, induction by an exogenous substance (xenobiotic) is typically intended. Induction of an enzyme typically results from induction of the gene encoding the enzyme.

A "nuclease-resistant" oligomeric molecule (oligomer) is one whose backbone is not susceptible to nuclease cleavage. Exemplary nuclease-resistant antisense oligomers are oligonucleotide analogs, such as phosphorothioate and phosphate-amine DNA (pnDNA), both of which have a charged backbone, and methyl phosphonate, morpholino, and peptide nucleic acid (PNA) analogs, all of which have uncharged backbones.

The terms "antisense oligonucleotide" and "antisense oligomer" are used interchangeably and refer to an oligomer having a sequence of nucleotide bases and a subunit-to-subunit backbone that allows the antisense oligomer to hybridize to a target sequence in an RNA by Watson-Crick base pairing, to form an RNA: oligomer heteroduplex within the target sequence. The oligomer may have exact sequence complementarity to the target sequence or near complementarity. These antisense oligomers may block or inhibit translation of the mRNA containing the target sequence, and/or modify the processing of the mRNA to produce a splice variant of the mRNA. Antisense oligonucleotides which are double-stranded DNA binding agents may inhibit gene transcription.

An oligonucleotide or antisense oligomer "specifically hybridizes" to a target polynucleotide if the oligomer hybridizes to the target under physiological conditions, with a $T_m$ greater than 37° C., preferably at least 50° C., and more preferably at least 60° C., 80° C., or higher. Such hybridization preferably corresponds to stringent hybridization conditions, selected to be about 10° C. lower, and preferably about 5° C. lower than the thermal melting point (Tm) for the specific sequence at a defined ionic strength and pH. At a given ionic strength and pH, the Tm is the temperature at which 50% of a target sequence hybridizes to a complementary polynucleotide.

Polynucleotides are described as "complementary" to one another when hybridization occurs in an antiparallel configuration between two single-stranded polynucleotides. A double-stranded polynucleotide can be "complementary" to another polynucleotide, if hybridization can occur between one of the strands of the first polynucleotide and the second. Complementarity (the degree that one polynucleotide is complementary with another) is quantifiable in terms of the proportion of bases in opposing strands that are expected to form hydrogen bonds with each other, according to generally accepted base-pairing rules.

Although the antisense oligomer is not necessarily 100% complementary to the target, sequence, it is effective to stably and specifically bind to the target sequence such that expression of the target sequence is modulated. The appropriate length of the oligomer to allow stable, effective binding combined with good specificity is about 8 to 40 nucleotide base units, and preferably about 12–25 base units. Mismatches, if present, are less destabilizing toward the end regions of the hybrid duplex than in the center. Oligomer bases that allow degenerate base pairing with target bases are also contemplated, assuming base-pair specificity with the target is maintained.

A first sequence is an "antisense sequence" with respect to a second sequence if a polynucleotide whose sequence is the first sequence specifically hybridizes to a polynucleotide whose sequence is the second sequence.

A "base-specific intracellular binding event involving a target RNA" refers to the specific binding of an oligomer with a target RNA sequence inside a cell even in the presence of many other diverse molecules. The base specificity of such binding is sequence specific. For example, a single-stranded polynucleotide can specifically bind to a single-stranded polynucleotide that is complementary in sequence.

As used herein, a "morpholino oligomer" or "morpholino oligonucleotide" refers to a polymeric molecule having a backbone which supports bases capable of hydrogen bonding to typical polynucleotides, wherein the polymer lacks the ribose backbone linked by phosphodiester bonds which is typical of nucleotides and nucleosides, and instead contains a subunit with a ring nitrogen with coupling through the ring nitrogen. A preferred "morpholino" oligonucleotide is composed of morpholino subunit structures of the form shown in FIGS. 5A–E, where (i) the structures are linked together by phosphorous-containing linkages, one to three atoms long, joining the morpholino nitrogen of one subunit to the 5' exocyclic carbon of an adjacent subunit, and (ii) Pi and Pj are purine or pyrimidine base-pairing moieties effective to bind, by base-specific hydrogen bonding, to a base in a polynucleotide. Exemplary structures for antisense oligonucleotides for use in the invention include the morpholino subunit types shown in FIGS. 5A–E, with the linkages shown in FIGS. 6A—A to 6E—E. The synthesis, structures, and binding characteristics of morpholino oligomers, including antisense oligomers, are described in detail in co-owned U.S. Pat. Nos. 5,185,444, 5,698,685, 5,217,866, 5,142,047, 5,034,506, 5,166,315, 5,521,063, and 5,506,337, all of which are incorporated herein by reference.

A preferred morpholino oligonucleotide is composed of morpholino subunit structures of the form shown in FIG. 2B—B, where the structures are linked together by phosphorodiamidate linkages, joining the morpholino nitrogen of one subunit to the 5' exocyclic carbon of an adjacent subunit, Pi and Pj are purine or pyrimidine base-pairing moieties effective to bind, by base-specific hydrogen bonding, to a base in a polynucleotide, X=NH2 or NHR, Y=O, and Z=O, where R is lower alkyl (i.e. C1 to C6, preferably C1 to C4 alkyl). Such structures are described, for example, in Hudziak et al., *Antisense Nucleic Acid Drug Dev.* 6, 267–272 (1996) and Summerton and Weller, *Antisense Nucleic Acid Drug Dev.* 7, 187–195 (1997). Unless otherwise indicated, "PMO"s referred to herein have this structure, where X is $NH_2$. Also preferred are structures having an alternate phosphorodiamidate linkage, where, in FIG. 2B—B, X=OR, Y=NH or NR, and Z=O.

A "C-5-methyl modified" oligonucleotide is one in which the C-5 hydrogen of cytidine bases has been replaced with a methyl group. A "C-5-propyne modified" or "C-5-propyne pyrimidine-modified" oligonucleotide is one in which the C-5 methyl group of thymidine bases and/or the C-5 hydrogen of cytidine bases has been replaced with a propynyl group ($-C\equiv C-CH_3$).

The term "modulating expression" relative to oligonucleotides refers to the ability of an antisense oligomer to either enhance or reduce the expression of a given protein by interfering with the expression or translation of RNA. In the case of enhanced protein expression, the antisense oligomer may block expression of a suppressor gene, e.g., a tumor suppressor gene. In the case of reduced protein expression, the antisense oligomer may directly block expression of a given gene, or contribute to the accelerated breakdown of the RNA transcribed from that gene.

An "effective amount" relative to an antisense oligomer refers to the amount of antisense oligomer administered to a mammalian subject, either as a single dose or as part of a series of doses, that is effective to specifically hybridize to all or part of a selected target sequence, thereby reducing expression of the protein encoded by the target sequence. "Treatment" of an individual or a cell is any type of intervention in an attempt to alter the natural course of the individual or cell. Treatment includes, but is not limited to, administration of a pharmaceutical composition, and may be performed either prophylactically or subsequent to the initiation of a pathologic event or contact with an etiologic agent.

The term "relative amount" is used where a comparison is made between a test measurement and a control measurement. The relative amount of a reagent forming a complex in a reaction is the amount reacting with a test specimen, compared with the amount reacting with a control specimen. The control specimen may be run separately in the same assay, or it may be part of the same sample (for example, normal tissue surrounding a malignant area in a tissue section).

"Coadministration" of an antisense oligomer with a drug may be concurrent with, following, or, preferably, preceding administration with the drug, as long as the antisense oligomer is effective to modulate the metabolism and enhance the efficacy of the drug.

Abbreviations: ON=oligonucleotide; ODN=oligodeoxyribonucleotide; PS or PS-ODN=phosphorothioate oligonucleotide; PMO=phosphoramidate or (preferably) phosphorodiamidate morpholino oligonucleotide.

II. Antisense Oligomers

Antisense oligomers effect changes in gene expression (transcription) and protein production (translation) by the complementary hybridization of relatively short oligonucleotides to single-stranded RNA or double-stranded DNA, such that the normal, essential functions of these intracellular nucleic acids are disrupted. (See, e.g., U.S. Pat. No. 5,843,684).

Two mechanisms of action of antisense oligomers on target nucleic acid molecules have been proposed. In one mechanism, antisense agents are thought to disrupt nucleic acid function via enzymatic cleavage of the targeted RNA by intracellular RNase H. The oligonucleotide or oligonucleotide analog, which must be of the deoxyribo type, hybridizes with the targeted RNA, and the duplex activates RNase H to cleave the RNA strand, thus destroying the normal function of the RNA. Phosphorothioate oligonucleotides are a prominent example of antisense oligomers that operate by this mechanism.

Another mechanism, termed "hybridization arrest", involves a terminating event in which the antisense oligomer binds to the target nucleic acid and thus prevents, by steric hindrance, the binding of essential proteins, most often ribosomes, to the nucleic acid. Exemplary antisense oligomers which act by this mechanism include methylphosphonate oligonucleotides and alpha anomer oligonucleotides. (See, e.g., Cohen, OLIGONUCLEOTIDES: ANTISENSE INHIBITORS OF GENE EXPRESSION, CRC Press, Inc., Boca Raton, Fla., 1989.)

The utility of antisense oligomers to modulate the pharmacokinetics of drugs or other xenobiotic agents, by decreasing production of specific metabolic enzymes which are induced by and/or metabolize these agents, requires that the oligomers be amenable to synthesis in large quantities, be taken up by cells and/or transported across cell membranes, hybridize appropriately to the targeted RNA (i.e., mRNA or pre-mRNA) and subsequently terminate or disrupt translation from the RNA.

Non-ionic oligonucleotide analogs, i.e., oligomers with uncharged backbones, generally cross cell membranes more readily than their charged counterparts. Non-ionic oligonucleotide analogs include phosphotriester- and methylphosphonate-linked DNA (Miller et al., *Biochemistry* 18:5134 (1979); Miller et al., *J. Biol. Chem.* 255:6959 (1980)), carbamate-linked nucleosides (Stirchak, E.P. et al., *J. Org. Chem.* 52:4202 (1987)), phosphoroamidate-linked DNA (Froehler et al., *Nucleic Acids Res.* 16:4831 (1988)), and peptide nucleic acids (PNAs).

A preferred nonionic antisense oligomer for use in the method of the invention is an uncharged-backbone morpholino oligomer as defined above. Morpholino oligomers, such as illustrated in FIGS. 5 and 6, are composed of morpholino subunit structures linked together by uncharged, phosphorous-containing linkages, one to three atoms long, joining the morpholino nitrogen of one subunit to the 5' exocyclic carbon of an adjacent subunit. Linked to each subunit is a purine or pyrimidine base-pairing moiety effective to bind, by base-specific hydrogen bonding, to a base in a polynucleotide. The pyrimidine base-pairing moieties may also include a C-5-propyne modification of thymidine and/or cytidine moieties, and/or a C-5-methyl modification of cytidine bases.

FIGS. 6AA–EE illustrate preferred backbone structures, showing two morpholino subunits of a multisubunit oligomer. Each ring structure includes a purine or pyrimidine or related hydrogen-bonding moiety, represented by $P_i$ and $P_j$, attached to the backbone morpholine moiety through a linkage in the β-orientation. The purine or pyrimidine base-pairing moieties in the oligomer are typically adenine, cytosine, guanine, uracil or thymine. In the structures of FIG. 5, the atom Y linking the 5' morpholino carbon to the phosphorous group may be sulfur, nitrogen, carbon, or oxygen; nitrogen and oxygen are preferred, and oxygen is particularly preferred. Z represents sulfur or oxygen, and is preferably oxygen. The X moiety pendant from the phosphorous may be any of the following: fluorine, alkyl or substituted alkyl, alkoxy or substituted alkoxy, thioalkoxy or substituted thioalkoxy, or unsubstituted, monosubstituted, or disubstituted nitrogen, including cyclic structures. Several cyclic disubstituted nitrogen moieties which are suitable for the X moiety are morpholine, pyrrole, and pyrazole. Preferred embodiments of X are alkoxy, amino ($NH_2$) and dialkyl-substituted nitrogen.

In preferred embodiments of FIG. 6B—B, Z is oxygen, Y is oxygen, and X is alkoxy (phosphoramidate linkage), or Z is oxygen, Y is oxygen, and X is unsubstituted, monosubstituted, or disubstituted nitrogen, including cyclic structures (phosphorodiamidate linkage). Also preferred are linkages in which Z is oxygen, Y is unsubstituted, monosubstituted, or disubstituted nitrogen, and X is alkoxy (alternate phosphorodiamidate linkage).

The solubility of the antisense compound, and the ability of the compound to resist precipitation on storage in solution, can be further enhanced by derivatizing the oligomer with a solubilizing moiety, such as a hydrophilic oligomer, or a charged moiety, such as a charged amino acid or organic acid. The moiety may be any biocompatible hydrophilic or charged moiety that can be coupled to the antisense compound and that does not interfere with compound binding to the target sequence. The moiety can be chemically attached to the antisense compound, e.g., at its 5' end, by well-known derivatization methods. One preferred moiety is a defined length oligo ethylene glycol moiety, such as triethylene glycol, coupled covalently to the 5' end of the antisense compound through a carbonate linkage, via a piperazine linking group forming a carbamate linkage with triethylene glycol, where the second piperazine nitrogen is coupled to the 5'-end phosphorodiamidate linkage of the antisense. Alternatively, or in addition, the compound may be designed to include one a small number of charged backbone linkages, such as a phosphodiester linkage, preferably near one of the ends of the compound. The added moiety is preferably effective to enhance solubility of the compound to at least about 30 mgs/ml, preferably at least 50 mgs/ml in aqueous medium. Antisense oligomers of the present invention can also include modifications including, but not limited to, conjugated moieties such as cholesterol; diamine compounds with varying numbers of carbon residues between the amino groups; and terminal ribose, deoxyribose and phosphate modifications which cleave or crosslink to hybridized target nucleic acids or to associated enzymes or other proteins which bind to the target nucleic acids.

Morpholino oligomers afford high target binding affinity, especially for RNA targets, and are resistant to degradation by nucleases. Binding of a morpholino oligomer to a target has been shown to give strong inactivation, due to the greater binding affinity noted above, and because the oligomer/target duplex is not susceptible to duplex unwinding mechanisms in the cell. Further, in therapeutic applications involving cellular uptake of the compound, the uncharged morpholino polymer is more efficiently transported into cells than are oligomers with charged backbones.

Although targeting of a messenger RNA sequence or an unspliced pre-mRNA sequence is preferred, a double-stranded DNA, i.e., a genomic DNA, may be targeted by using a non-ionic probe designed for sequence-specific binding to major-groove sites in duplex DNA. Oligomers suitable for forming base-specific triplex structures with a target duplex DNA are described, for example, in co-owned U.S. Pat. No. 5,405,938.

In vivo Effectiveness of Morpholino Oligomers. Morpholino oligonucleotides have been shown to provide significantly improved selectivity in inhibiting translation of targeted sequences in comparison to phosphorothioate oligonucleotides, which are widely used in the field. The morpholino oligomers have also been shown to inhibit translation at much lower concentrations than the corresponding phosphorothioates, and with little or no evidence of the substantial non-antisense activity exhibited by the phosphorothioates. See, for example, Summerton et al., *Antisense & Nucleic Acid Drug Dev* 7 (2) p63–70 (1997). Because the morpholino oligomers are uncharged, they are more effective at penetrating cell membranes. The morpholino oligomers were also reported to have very high nuclease resistance and good water solubility, making them good candidates for in vivo use.

The efficacy of morpholino antisense oligonucleotides in vivo is described in co-owned and copending U.S. provisional application Serial No. 60/117,846, filed Jan. 29, 1999. In the procedures described therein, a phosphoramidate morpholino oligonucleotide (PMO) forms a heteroduplex with target RNA, which is protected in this duplex state from nuclease degradation. The duplex is expelled from the cell, and the target RNA can later be detected in a body fluid sample, e.g. a urine sample, from the subject. These results demonstrate that the morpholino oligomers (i) migrate to and enter cells in the body and (ii) bind with high affinity, via Watson-Crick base-pairing, to target nucleic acid regions, (iii) be expelled from the cells into the bloodstream in the form of a nuclease-resistant heteroduplex, and (iv) survive in the bloodstream in sufficient amount for detection in a body fluid.

III. Selection of Target Genes

The present invention relates to a method of improving the pharmacokinetics of a drug administered to a subject, by reducing the production of a drug-metabolizing enzyme which is up-regulated either by the drug itself or by a xenobiotic agent to which the subject has been exposed. The drug-metabolizing enzyme may convert the drug into a toxic metabolite, reduce the half-life of the drug in the subject, or both. Transcription of target RNA from the enzyme gene (i.e., the "target gene") is induced by the drug, or by a different xenobiotic agent. According to the invention, a nuclease-resistant antisense oligomer, preferably a morpholino oligomer, is targeted to a gene encoding a drug-metabolizing enzyme which reduces the half-life of the drug, or converts the drug into a toxic metabolite, or both. The antisense oligomer, preferably co-administered with the drug, is effective to reduce production of the enzyme in the subject by hybridizing to the target RNA.

The production of any drug-metabolizing enzyme encoded by an endogenous xenobiotic-inducible gene may be decreased by the method of this invention. For example, important Phase 2 drug-metabolizing enzymes include epoxide hydrolases, whose substrates include carbamazepine- 10,11 -epoxide; glucuronyl transferases, whose substrates include oxazepam, and which are induced by anticonvulsant drugs such as phenytoin and carbamazepine; and glutathione transferases. Selection of the enzyme will be determined by the metabolic scheme of the drug in question.

A. The Cytochrome p450 Family

In accordance with a preferred embodiment, the present invention provides antisense oligomers which are antisense to cytochrome p450 (CYp450) genes. The cytochrome p450s are a collection of enzymes involved in the oxidative metabolism of both endogenous and exogenous compounds. Over 200 genes encoding cytochrome p450, divided among over 30 gene families, have been identified. The p450 gene families are organized into subfamilies, which vary in regulation of gene expression and in amino acid sequence homology, substrate specificity, catalytic activity, and physiological role of the encoded enzymes. The following discussion of representative p450 genes, inducers of those genes, and substrates of the encoded enzymes, is provided for illustrative purposes and is not intended to limit the invention.

Sequences for numerous p450 genes of various species are known and available to those of skill in the art through public databases such as GenBank and review articles such as F. J. Gonzales, "The Molecular Biology of Cytochrome p450's", *Pharmacological Reviews* 40(4), 243–288 (1989); S. D. Black et al., "P-450 Cytochromes: Structure and Function," *Adv. Enzymol. Relat. Areas Mol. Biol.* 60, 35–87 (1987); D. R. Nelson et al., "The p450 Superfamily: Update on New Sequences, Gene Mapping, Accession Numbers, Early Trivial Names of Enzymes, and Nomenclature," *DNA Cell Biol.* 12(1),1–51 (January–February 1993), and articles cited therein.

B. Sequence Homology of p450 Enzymes and Genes

High levels of sequence homology have been found among p450 enzymes and their genes in different mammalian species. For example, the rat, human and rabbit 2E1 cDNAs have been isolated and sequenced, and their amino acid sequences exhibit about 80% similarity. The human 2B subfamily cDNAs were isolated by screening liver libraries with rat 2B cDNA probes, and the isolated cDNAs demonstrated >75% amino acid similarity. The rat CYP3A enzymes, CYP3A1 and CYP3A2, are approximately 90% identical and functionally equivalent to human CYPs 3A3 and 3A4, respectively (Desjardins and Iversen, *J. Pharmacol. Exp. Ther.* 275(3):1608–13, 1995). The following table shows sequence similarities among the ATG regions of mRNA from CYP3A genes of these and other species.

TABLE 1

| Species | p450 Gene | GenBank Accession No. | Sequence (5' → 3') | SEQ ID NO: |
|---|---|---|---|---|
| Rat | CYP3A2 | U09742<br>X62087<br>S45634 | GAC AGA CAA GCA GGG ATG GAC CTG CTT TCA GCT | 1 |

TABLE 1-continued

| Species | p450 Gene | GenBank Accession No. | Sequence (5' → 3') | SEQ ID NO: |
|---|---|---|---|---|
| Mouse | CYP3A16 | D26137 | GAC AGA CAA GCA GAG ATG AAC CTA TTT TCA GCG | 2 |
| Mouse | CYP3A16 | X63023 | TTA AAG AAA ACA GCA ATG GAC CTG ATC CCA AAC | 3 |
| Mouse | CYP3AM1 | X60452 | GAC AAA CAA GCA GGG ATG GAC CTG GTT TTC AGC | 4 |
| Hamster | CYP3A | D16363 | AAA TCG CAC AAG GAA ATG GAC CTG GTC CCC AGC | 5 |
| Rabbit | CYP3A6 | J05034 | AGA AGG ACA GTG GCG ATG GAT CTG ATC TTT TCC | 6 |
| Dog | CYP3A12 | X54915 | AGA GGA CGA GTG GTC ATG GAC TTC ATC CCA AGC | 7 |
| Pig | CYP3A39 | Z93099 | ACG AGG ACA GTG GCC ATG GAC CTG ATC CCA GGC | 8 |
| Goat | CYP3A24 | U59378 | GCC AAG AAA GTG GCC ATG GAG CTG ATC CCA AGT | 9 |
| Monkey | CYP3A | S53047 | GGA AGG AAA GTA GTG ATG GAT CTC ATC CCA GAC | 10 |
| Human | CYP3A3 | X12387 M13785 D00003 | GTA AGG AAA GTA GTG ATG GCT CTC ATC CCA GAC | 11 |
| Human | CYP3A4 | M14096 | GTA AGG AAA GTA GTG ATG GCT CTC ATC CCA GAC | 12 |
| Human | CYP3A5 | J04813 | AGA AGG AAA GTG GCG ATG GAC CTC ATC CCA AAT | 13 |
| Human | CYP3A5A | L35912 | AGA AGG CAA GTG GCG ATG GAC CTC ATC CCA AAT | 14 |
| Human | CYP3A7 | D00408 | GTG ATG GAT CTC ATC CCA AAC | 15 |

The following degrees of homology were found in three conserved domains of the p4503A proteins:

1. Heme-binding cysteine-containing peptide; the fifth ligand to heme iron (23 amino acid segment starting at position 435 in human protein)

| Dog | 21/23 | 91.3% similarity to human protein |
| Rat | 23/23 | 100% |
| Mouse | 22/23 | 95.7% |
| Monkey | 21/23 | 91.3% |
| Pig | 22/23 | 95.7% |
| Rabbit | 20/23 | 87.0% |

2. Membrane transition binding domain (8 amino acid segment starting at position 39 in human protein)

| Dog | 8/8 | 100% similarity to human protein |
| Rat | 7/8 | 87.5% |
| Mouse | 7/8 | 87.5% |
| Monkey | 7/8 | 87.5% |
| Pig | 7/8 | 87.5% |
| Rabbit | 8/8 | 100% |

3. Signal sequence and half-transfer sequence for membrane insertion (20 amino acid segment starting at position 167 in human protein)

| Dog | 17/20 | 85% similarity to human protein |
| Rat | 18/20 | 90% |
| Mouse | 18/20 | 90% |
| Monkey | 20/20 | 100% |
| Pig | 19/20 | 95% |
| Rabbit | 16/20 | 80% |
| Goat | 16/20 | 80% |
| Guinea pig | 13/20 | 65% |

The average degree of homology over these three known functional domains (51 amino acids of 500 total) was 92.9% human to monkey, 92.5% human to rat, and 92.1% human to dog.

C. Substrates and Inducers of p450 Enzymes

Genes in the CYP2B subfamily are known to be strongly induced by phenobarbital. The 2B1 and 2B2 proteins exhibit 97% amino acid similarity. These enzymes have similar substrate specificities; however, purified 2B1 (rat) has about a 5-fold higher catalytic activity than 2B2 for certain substrates, including benzphetamine and testosterone, and a two-fold to three-fold higher activity for the substrates benzo[a]pyrene and 7,12-dimethylbenzanthracene.

A distinct ethanol-inducible form of p450, CYP2E1, was first identified in rabbits and later in rats and humans. The enzymes of this subfamily metabolize a large number of substrates, as shown below, including, for example, ethanol, acetone, acetoacetate, acetol, diethyl ether, p-nitrophenol, halothane, benzene, pyridine, and N-nitrosodimethylamine.

The CYP3A subfamily is involved in the 6β-hydroxylation of testosterone and in the metabolism of numerous clinically important drugs, such as those listed below.

Listed below are further examples of known inducers and substrates of members of various p450 subfamilies. See also the discussion in Klassen, ed., *Casarett and Doull's Toxicology: The Basis Science of Poisons*, McGraw-Hill, 1996, pp. 150 ff. Further information about cytochrome p450 substrates, inducers, and metabolites can be found in Gonzales and other review articles cited above. Current information sources available via the Internet include the "Cytochrome p450 Homepage", maintained by David Nelson, the "Cytochrome p450 Database", provided by the Institute of Biomedical Chemistry & Center for Molecular Design, and the "Directory of p450-containing Systems", provided by Kirill N. Degtyarenko and Péter Fábián.

The exemplary p450 genes discussed herein are given for illustrative purposes only and are not intended to limit the invention.

p450 family 1 (CYP1)
CYP1A1:
  inducers include: dioxin, PAH (polycyclic aromatic hydrocarbons) in tobacco smoke or charcoal-broiled beef, β-naphthoflavone in food
  substrates include: diethylstilbestrol, 2- and 4-hydroxyestradiol
CYP1A2:
  inducers include: dioxin, PAH, β-naphthoflavone, cruciferous vegetables, omeprazole substrates include: acetaminophen, phenacetin, acetanilide (analgesics), caffeine, clozapine (sedative), cyclobenzaprine (muscle relaxant), estradiol, imipramine (antidepressant), mexillitene (antiarrhythmic), naproxen (analgesic), riluzole, tacrine, theophylline (cardiac stimulant, bronchodilator, smooth muscle relaxant), warfarin.
  probe reaction: caffeine 3-demethylation p450 family 2 (CYP2)
CYP2A6:
  inducers include: barbiturates
  substrates include: coumarin, butadiene, nicotine
CYP2B1:
  inducers include: phenobarbital
  substrates include: phenobarbital, hexobarbital
CYP2C9:
  inducers include: rifampin, secobarbital
  substrates include: NSAIDs such as diclofenac, ibuprofen, and piroxicam; oral hypoglycemic agents such as tolbutamide and glipizide; angiotensin-2 blockers such as irbesartan, losartan, and valsartan; naproxen (analgesic); phenytoin (anticonvulsant, antiepileptic); sulfamethoxazole, tamoxifen (antineoplastic); torsemide; warfarin
CYP2C19:
  inducers include: rifampin, secobarbital
  substrates include: hexobarbital, mephobarbital, imipramine, clomipramine, citalopram, cycloguanil, the anti-epileptics phenytoin and diazepam, S-mephenytoin, diphenylhydantoin, lansoprazole, pantoprazole, omeprazole, pentamidine, propranolol, cyclophosphamide, progesterone
CYP2D6:
  inducers include: dexamethasone, rifampin
  substrates include: antidepressants (imipramine, clomipramine, desimpramine), antipsychotics (haloperidol, perphenazine, risperidone, thioridazine), beta blockers (carvedilol, S-metoprolol, propafenone, timolol), amphetamine, codeine, dextromethorphan, fluoxetine, S-mexilletine, phenacetin, propranolol
CYP2E1:
  inducers include: ethanol, acetone, isoniazid, dimethyl sulfoxide, pyrazoles.
  substrates include: acetaminophen; chlorzoxazone (muscle relaxant), ethanol; caffiene, theophylline; dapsone, general anesthetics such as enflurane, halothane, and methoxyflurane; nitrosamines ps 450 family 3 (CYP3)

CYP3A1, CYP3A2: rat CYP3A subfamily; approximately 90% identical and functionally equivalent to human CYP3A3 and CYP3A4, respectively (below)
CYP3A4:
  inducers include: carbamazepine, phenobarbital, phenytoin, dexamethasone and other glucocorticoids; barbiturates, various steroids, antibiotics such as rifampin, rifabutin, erythromycin; phenylbutazone, sulfadimidine, sulfinpyrazone, troleandomycin
  substrates include: HIV Protease Inhibitors such as indinavir, ritonavir, and saquinavir; benzodiazepines such as alprazolam, diazepam, midazolam, and triazolam; immune modulators such as cyclosporine; antihistamines such as astemizole and chlorpheniramine; HMG CoA Reductase inhibitors such as atorvastatin, cerivastatin, lovastatin, and simvastatin; channel blockers such as diltiazem, felodipine, nifedipine, nisoldipine, nitrendipine, and verapamil; antibiotics such as clarithromycin, erythromycin, and rapamycin; various steroids including cortisol, testosterone, progesterone, estradiol, ethinylestradiol, hydrocortisone, prednisone, and prednisolone; acetominophen, aldrin, alfentanil, amiodarone, astemizole, benzphetamine, budesonide, carbemazepine, cyclophosphamide, ifosphamide, dapsone, digitoxin, quinidine (antiarrhythmic), etoposide, flutamide, imipramine, lansoprazole, lidocaine, losartan, omeprazole, retinoic acid, FK506 (tacrolimus), tamoxifen, taxol, teniposide, terfenadine, buspirone, haloperidol (antipsychotic), methadone, sildenafil, trazodone, theophylline, toremifine, troleandomycin, warfarin, zatosetron, zonisamide.

Figure 2:
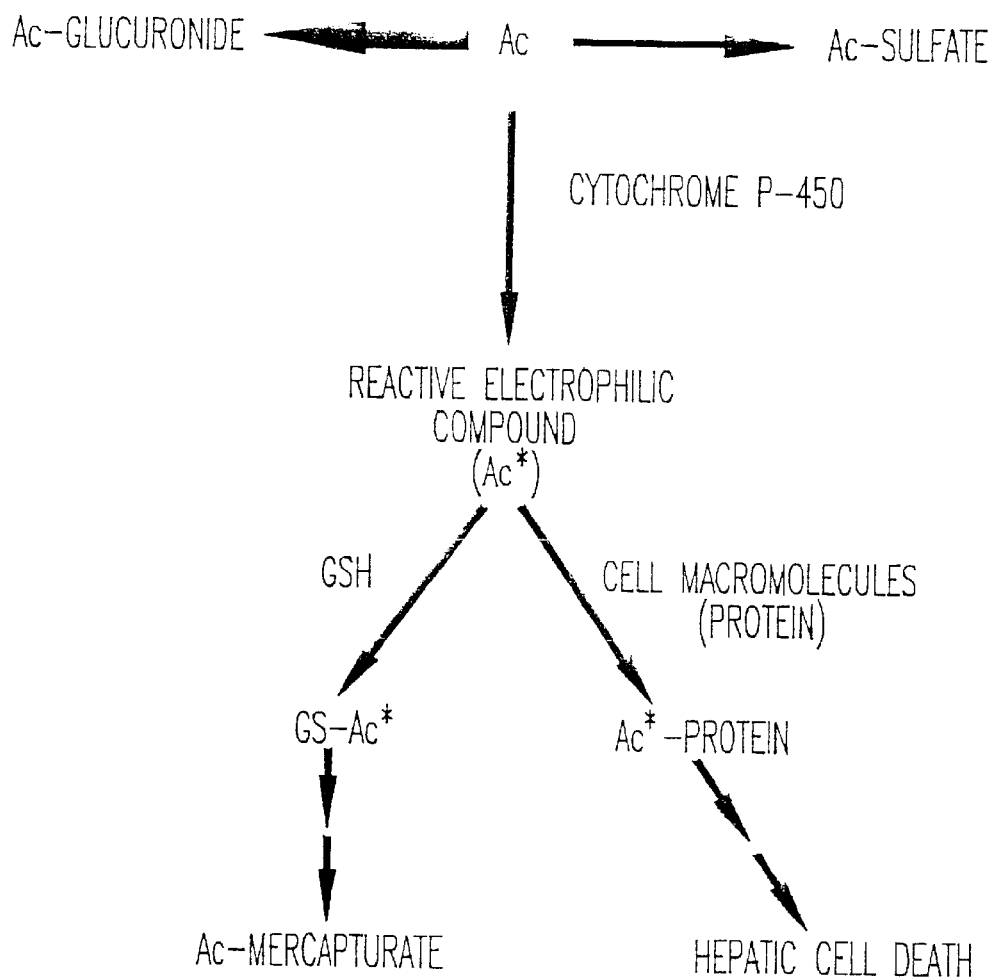
FIG. 2 shows alternative pathways for acetaminophen metabolism, leading to a toxic product or to a non-toxic mercapturate conjugate, where GSH=glutathione and AC*= reactive intermediate.

450 family 6 (CYP6)
CYP6A1:
  inducers include: chlofibrate
  substrates include: fatty acids D. Exemplary Drugs Metabolized by p450 Enzymes Acetaminophen: Ethanol up-regulates CYP2E1, which metabolizes acetaminophen to a reactive quinone (FIG. 2). This reactive quinone intermediate, when produced in sufficient amounts, causes liver damage and necrosis. An oligomer antisense to the CYP2E1 gene reduces synthesis of the enzyme and decreases production of the toxic intermediate. Reducing the flux through the toxic pathway enables alternative, more desirable metabolic pathways to compensate.

Sedatives: The sedative phenobarbital (PB) up-regulates several p450 genes, including those of the CYP2B and CYP3A subfamilies. Upregulation of these enzymes increases the metabolism and reduces the sedative effects of PB and the related sedative hexobarbital. Example 1 demonstrates that an antisense oligonucleotide to the CYP2B1 gene reduces synthesis of the enzyme and decreases HB metabolism, enabling lower amounts of HB be administered for the equivalent sedative effect. Such oligomers also increased the effectiveness of HB in the presence of the inducing agent phenobarbital. Example 3 demonstrates a similar effect of antisense to CYP3A2 on efficacy of midazolam (MZ).

Antibiotics: The antibiotics rifampicin, rifampin, rifabutin, erythromycin, and related compounds are inducers of the CYP3A4 gene and are substrates of the enzyme product. An oligomer antisense to the CYP3A4 gene increases the serum half-life and hence the effectiveness of the antibiotic.

Oral contraceptive/estrogen replacement therapy: Estrogens and estradiols are the active ingredients in oral contraceptives and in hormonal replacement therapies for postmenopausal women. Women who are also taking antibiotics such as rifampicin or erythromycin, or glucocorticoids such as dexamethasone, or who smoke, risk decreased efficacy of the estrogen/estradiol treatments due to increased metabolism of these compounds by up-regulated CYP3A4 and/or CYP1A2 enzymes. Administration of oligomers antisense to the CYP3A4 and/or CYP1A2 genes in such situations block up-regulation of these enzymes and reduces risk of pregnancy in women taking oral contraceptives, or of osteoporosis in women receiving estrogen replacement therapy.

Protease Inhibitors: All protease inhibitors and non-nucleoside reverse transcriptase inhibitors currently indicated for use in treatment of HIV are substrates of p450 enzymes; in particular, they are metabolized by CYP3A4 enzymes (see e.g. Sahai, *AIDS* 10 Suppl 1:S21–5, 1996) with possible participation by CYP2D6 enzymes (Kumar et al., *J. Pharmacol. Exp. Ther.* 277(1):423–31, 1996). Although protease inhibitors are reported to be inhibitors of CYP3A4, some non-nucleoside reverse transcriptase inhibitors, such as nevirapine and efavirenz, are inducers of CYP3A4 (see e.g. Murphy et al., *Expert Opin Invest Drugs* 5/9: 1183–99, 1996). Given the increasing use of multidrug therapy for treatment of HIV infection, the potential for interference is high. Supplemental administration of oligomers antisense to CYP3A4 and/or CYP2D6 genes can block up-regulation of these enzymes, thus reducing the metabolism of the protease inhibitors, allowing for lower doses and reduction of sometimes serious side effects.

IV. Design and Preparation of Antisense Oligomers
A. Selection of Target Sequences Target sequences, including genomic sequences, pre-mRNA, mRNA, and/or cDNA sequences, from genes selected according to the considerations outlined in the previous sections, may be obtained from the GenBank sequence database or from other published sources readily available to those of skill in the art. As noted above, sequences for numerous rat and human p450 genes are known and available to those of skill in the art through sources such as GenBank and review articles such as Gonzales 1989, Black et al. 1987, and Nelson et al. 1993, cited above. For example, Nelson et al. lists all database accession numbers for p450 genes that were available in the GenBank/EMBL, SwissProt, and NBRF-PIR databases as of December 1992. Accession numbers for human p450 sequences are included from the following families: CYP-1A1, 1A2, 2A6, 2A7, 2B6, 2B7P, 2C8, 2C9, 2C10, 2C17, 2C18, 2C19, 2D6, 2D7P, 2D8P, 2E1, 2F1, 3A3, 3A4, 3A5, 3A7, 4A9, 4A11, 4B1, 4F2, 4F3, 5, 7, 11A1, 11B1, 17, 19, 21A1P, 21A2, and 27. Since the publication of the 1993 article, other human sequences, such as those for CYP-1B1 and CYP-2B1, have also been made available in GenBank.

B. Length and Complementarity of the Antisense Oligomer

The appropriate length of the antisense oligomer to allow stable, effective binding combined with good specificity is about generally 10 to 40 nucleotide base units, and preferably about 15 to 25 base units. The antisense oligomer may be 100% complementary to a desired region of the target sequence, or it may include mismatches, e.g., to accommodate coding sequence variants, such as polymorphisms, as long as the duplex formed between the oligomer and target RNA is sufficiently stable in the cell to block or inhibit translation. Mismatches, if present, are less destabilizing toward the end regions of the hybrid duplex than in the middle. The number of mismatches allowed will depend on the length of the oligomer, the percentage of G:C basepair in the duplex and the position of the mismatch(es) in the duplex, according to well understood principles of duplex stability. Preferably, the $T_m$ of the oligomer/target sequence will be at least 37° C., more preferably at least 50° C., and most preferably at least 60° C., 80° C., or higher. Oligomer bases that allow degenerate base pairing with target bases are also contemplated, assuming base-pair specificity with the target is maintained.

C. Exemplary Antisense Oligomers Targeting p450

Exemplary oligomer sequences can be designed according to the following guidelines:

1. Each oligomer either (a) spans the AUG start codon of the indicated gene, with the CAU complement of the start codon (expressed in a 5' to 3' direction) being positioned near the center or near the 3' end of the oligomer, or (b) spans an intron-exon (splice donor) boundary or, more preferably, an exon-intron (splice acceptor) boundary of an unspliced pre-mRNA sequence;

2. has a length of about 20–25 bases; and 3. preferably terminates, at the 5' end, at a G (guanine) base, which confers stability to the duplex.

Exemplary antisense oligomers having the base sequences shown in Table 2 are designed for p450 RNA-specific inhibition of translation and/or splicing. The location of the bases in the target sequence which hybridize with the oligomer, numbered according to the GenBank sequence numbering, is indicated at the right in the table. By convention, the orientation of the antisense sequences is shown in a 5' to 3' direction. In a hybrid duplex in which the target gene sequence is shown a 5' to 3' direction (by convention), the orientation of the hybridized antisense oligomer sequence would be reversed; that is in a 3' to 5' direction. The table also identifies the sequence identifier number (SEQ ID NO:) of each exemplary oligomer sequence. Preferred antisense oligomers for use in practicing the method of the invention are those identified by SEQ ID NOs: 16–17, 19, 25, 27, 30, 34–35 and 46–47, for inhibiting translation and/or splicing of target RNAs derived from the rat CYP2B1, CYP2E1, and CYP3A2 and human CYP1A2, CYP2B1, CYP2E1, and CYP3A4 genes, respectively.

TABLE 2

| p450 Gene | GenBank Acc. No. | Antisense Sequence (5' -> 3') | SEQ ID NO | Site Targeted | Posn. in sequence |
|---|---|---|---|---|---|
| CYP2B1 (rat) | M11251 | GGAGCAAGATACTGGGCTCCAT | 16 | ATG start | 490- |
|  | J00719 | AAAGAAGAGAGAGAGCAGGGAG | 17 | downstream of ATG | 855- |
| CYP2E1 | M20131 | GGTTTATTATTAGCTGCAGTTGGCT ATCAT | 18 | upstream of ATG | 1406- |

TABLE 2-continued

| p450 Gene | GenBank Acc. No. | Antisense Sequence (5' -> 3') | SEQ ID NO | Site Targeted | Posn. in sequence |
|---|---|---|---|---|---|
| | | CCAAGAACCGC<u>CAT</u>GGTGCC | 19 | ATG start | 1560- |
| | | ACCTTGGTGAAAGACTTGGG | 20 | exon 1 splice donor | 1725- |
| | | CCTTGTTCTTGTACTCCTGG | 21 | exon 2 splice donor | 2645- |
| | | GAGAAGCATGGTCACCTGGA | 22 | exon 4 splice donor | 6681- |
| | | CCAACACACACACGCTTTCC | 23 | exon 9 splice acceptor | 11591- |
| CYP3A2 | U09742 | TGAGAGCTGAAAGCAGGTC<u>CAT</u> | 24 | ATG start | 69- |
| | | GAGCTGAAAGCAGGTC<u>CAT</u>CCC | 25 | " | 66- |
| CYP1A1 (human) | K03191 | ATTGGGAAAAG<u>CAT</u>GATCAG | 26 | ATG start | 81- |
| CYP1A2 | L00384 M14337 | TGGGACAATGC<u>CAT</u>CTGTAC | 27 | " | 9- |
| CYP1B1 | U03688 | AGGCTGGTGCC<u>CAT</u>GCTGCG | 28 | " | 341- |
| CYP2A6 | M33318 M33316 | CCTGAGGCCAG<u>CAT</u>GGTGGT | 29 | " | 4- |
| CYP2B1 | M29874 J02864 | ACGCTGAGTTC<u>CAT</u>GGTCTG | 30 | " | 1- |
| CYF2C9 | M61855 J05326 | ACAAGAGAATC<u>CAT</u>TGAAGC | 31 | " | 7- |
| CYP2C19 | M61854 J05326 | CACAAAAGGATC<u>CAT</u>TGAAG | 32 | " | 1- |
| CYP2D6 | M33388 | GCTTCTAGCCC<u>CAT</u>ACCTGC | 33 | " | 1614- |
| CYP2E1 | J02843 | CCGAGGGCAGA<u>CAT</u>GGTGCC | 34 | " | 2819- |
| CYP3A4 | AF182273 | GTCTGGGATGAGAGC<u>CAT</u>CAC | 35 | " | 7- |
| | | CTGGGATGAGAGC<u>CAT</u>CAC | 46 | " | 7- |
| | | CTGGGATGAGAGC<u>CAT</u>CACT | 47 | " | 6- |

E. Testing the Effectiveness of the Antisense Oligomers

The effectiveness of a given antisense oligomer molecule in inhibiting expression of the target gene may be determined by screening methods known in the art.

E1. In vitro screening methods: Candidate antisense oligomers can be tested in vitro in, for example, hepatocyte cell culture, to quantify the effect of the oligomer on protein produced by the target RNA in the presence and absence of drugs or other inducers. See, for example, Examples 2 and 4 below. RNA quantitation methods are known in the art, and include Northern blot and RT-PCR assays. Protein production can be evaluated by Western blot or ELISA using antibodies specific for the target enzyme. Alternatively or in addition, protein expression can be evaluated enzymatically using probe substrates specific for the target enzyme. For example, substrates are known which differentially react with various p450 isozymes (M. Burke et al., *Biochem. Pharmacol.* 34(18):3337–45 (1985); Gonzalez, 1989 (cited above)).

Candidate oligomers are also evaluated, according to well known methods, for acute and chronic cellular toxicity, such as the effect on overall protein and DNA synthesis as measured via incorporation of $^3$H-leucine and $^3$H-thymidine, respectively.

It is desirable that non-specific binding of the oligomeric molecule to non-target sequences is limited. To test for non-specific binding effects, control sequences such as sense or nonsense sequences, or sequences containing mismatched bases, may be included in screening tests. Excess targeted protein or mRNA may also be added to the cell culture to determine if the effect of the antisense oligomer is reversed.

E2. In vivo screening methods: Antisense compositions may be tested in vivo in animal models as described, for example, in Examples 1, 3, and 5 below. Effects of a drug can be observed directly, as in sleep time induced by hexobarbital, and/or enzyme levels can be determined by assays known in the art.

As described above and in copending and co-owned U.S. application Ser. No. 60/117,846, duplexes of PMO antisense oligomers with target RNA sequences have been detected in body fluid samples following in vivo administration of the PMO oligomers. Such methods could be employed for in vivo screening of target RNA binding of a given oligonucleotide.

V. Pharmacokinetics and Administration

The pharmacokinetics of nuclease-resistant oligonucleotides has been shown to be favorable for in vivo therapeutic treatment of various endogenous genes. To date, studies in the rat, mouse and monkey reveal an elimination half-life in plasma longer than twenty hours. It has also been shown that the liver, where most drug metabolism occurs, is an organ of accumulation for oligonucleotides. See, for example, P. Iversen et al., *Antisense Res & Dev* 4: 43–52 (1994) and E. Bayever et al., *Antisense Res and Dev* 3:383–390 (1993), for discussions of the pharmacokinetics of phosphorothioate oligonucleotides administered to animal subjects and to human patients. Bayever et al. conclude that safety and favorable pharnacokinetics support further investigations of phosphorothioate oligonucleotides as potential gene specific therapeutic agents in humans.

In a preferred embodiment of the present method, the antisense oligonucleotide is a morpholino oligonucleotide, particularly a phosphoramidate- or phosphorodiamidate-linked morpholino oligonucleotide (PMO). These molecules have been shown to provide significantly improved selectivity in inhibiting translation of targeted sequences in comparison to the widely used phosphorothioates. The morpholino oligomers were also shown to inhibit translation at much lower concentrations than the corresponding phosphorothioates, and with little or no evidence of the non-antisense activity often exhibited by phosphorothioates.

See, for example, Summerton et al., *Antisense & Nucleic Acid Drug Dev* 7(2):63–70 (April 1997). Because the morpholino oligomers are uncharged, they are more effective at penetrating cell membranes. The morpholino oligomers also have high nuclease resistance and good water solubility, making them good candidates for in vivo use.

Table 3 compares pharmacokinetic and renal excretion properties of phosphorothioate (PS) and PMO oligonucleotides, such as those shown in Table 8 below, after IP injection of a single 0.1 mg dose.

TABLE 3

Single Dose (0.1 mg) Plasma Pharmacokinetics

|  | PS | PMO |
|---|---|---|
| Pharmacokinetic Properties | | |
| Half-life | 7.8 ± 3.8 hrs | 7.1 ± 1.9 hrs |
| Volume of Distribution | 1.2 ± 0.3 liters/kg | 1.5 ± 0.2 liters/kg |
| Area Under Curve | 245.4 ± 13.3 µg · min/ml | 337 ± 67 µg · min/ml |
| Plasma Clearance | 0.43 ± 0.02 ml/min | 1.2 ± 0.3 ml/min |
| Renal Excretion Properties | | |
| Excretion Rate | 4.8 ± 0.6 ng/min | 15.9 ± 3.1 ng/min |
| Renal Clearance | 3.4 ± 1.5 ml/min | 0.75 ± 0.18 ml/min |

Routes of administration of antisense oligomers include, but are not limited to, various systemic routes, including oral and parenteral routes, e.g., intravenous, subcutaneous, intraperitoneal, intramuscular, and intraarterial injection, as well as inhalation and transdermal delivery. In some cases, targeted delivery by direct administration to a particular tissue or site is preferred. It is appreciated that any methods which are effective to deliver the drug to a target site or to introduce the drug into the bloodstream are also contemplated.

Examples of standard pharmaceutically accepted carriers include saline, phosphate buffered saline (PBS), water, aqueous ethanol, emulsions such as oil/water emulsions, triglyceride emulsions, wetting agents, tablets and capsules. It will be understood that the choice of suitable physiologically acceptable carrier will vary dependent upon the chosen mode of administration.

Molecular conjugates useful for delivering antisense morpholino oligomers are described in U.S. Pat. No. 6,030,941 (Summerton and Weller, 2000), which is incorporated herein by reference. The oligomers of the invention may also be administered encapsulated in liposomes. (See, e.g., Williams, S. A., *Leukemia* 10(12):1980–1989, 1996; Lappalainen et al., *Antiviral Res.* 23:119, 1994; Uhlmann et al., "Antisense Oligonucleotides: A New Therapeutic Principle", in *Chemical Reviews*, Volume 90, No. 4, pp 544–584, 1990; Gregoriadis, G., Chapter 14, "Liposomes", in *Drug Carriers in Biology and Medicine*, pp 287–341, Academic Press, 1979.) The active ingredient, depending upon its solubility, may be present both in the aqueous phase and in the lipidic layer(s), or in what is generally termed a liposomic suspension. The lipidic layer generally comprises phospholipids, such as lecithin or sphingomyelin, steroids such as cholesterol, ionic surfactants such as diacetylphosphate, stearylamine, or phosphatidic acid, and/or other hydrophobic materials. The diameters of the liposomes generally range from about 15 nm to about 5 microns.

In practicing the method of the invention, the antisense oligomer is co-administered with the drug at a desired dose and dosing schedule. Preferably, the oligonucleotide is first administered several hours to several days before first administering the drug, to allow reduction of the target enzyme level. Preferred doses for oral administration are between about 1–2 mg oligomer/kg patient body weight, assuming an oligonucleotide MW of about 7000. A typical therapeutic dose for a patient weight 70 kg would thus be about 70 mg administered once a day, although higher doses may be administered if needed. For IV administration, the preferred doses are about ⅓ the oral dose.

The dose may be administered once several times daily, once daily, or less often, e.g., for prophylactic purposes. The efficacy of treatment may be followed by established tests, according to the drug whose metabolism is being modulated. Typically, the oligonucleotide will be administered at least once daily for a period of time concurrent with the administration of the drug, and may be discontinued, for example, when the drug therapy is discontinued.

A. Oral Administration

In a preferred embodiment, the morpholino oligomer is delivered orally. The oral bioavailability of antisense PMOs was demonstrated in rats, using a PMO antisense to rat CYP3A2 (SEQ ID NO: 25), as described in Example 5 below. The antisense PMO (2 mg/kg body weight) was administered to rats by oral gavage, and organs were harvested 24 hours later. A Western blot of liver microsome samples (FIG. 7, Lanes 4 and 5) showed a reduction in CYP3A2 protein greater than that obtained using 25% of this dose administered intraperitoneally.

B. Transdermal Administration

In another preferred embodiment, the morpholino oligomer is administered transdermally. Transdermal delivery of antisense oligomers may be accomplished by use of a pharmaceutically acceptable carrier adapted for topical administration, or by use of a transdermal patch. Such carriers typically include an aqueous or alcoholic solvent and one or more transdermal penetration enhancers, many of which are known in the art. See, for example, *Pharmaceutical Skin Penetration Enhancement*, K. A. Walters and J. Hadgraft, Eds. (Dekker, New York, 1993); *Drug Permeation Enhancement: Theory and Applications*, D. S. Hseih, Ed. (Dekker, New York, 1994). Examples include diols (e.g. glycerol, propylene glycol), polyethylene glycol, polypropylene glycol and sorbitan esters thereof, fatty alcohols, fatty acids, fatty acid amides, fatty acid esters (e.g. glycerol monooleate, glycerol monolinoleate, isopropyl isostearate, isopropyl linoleate, isopropyl myristate, isopropyl palmitate, sorbitan laurates and oleates), trimethylene glycol, fatty alcohol ethers, Tween® 20, 40, 60, 80, and 85, cyclodextrins, nicotinic esters, amino acids, lecithins, terpenes such as limonene or menthol, ionic compounds such as ascorbate, fatty alkyl ammonium halides, monoalkyl phosphates, sodium hyaluronate, sodium 5-methoxysalicylate, and sodium deoxycholate, dimethyl sulfoxide and related compounds, N-methyl pyrrolidone and related compounds, and azone and related compounds (see e.g. Minaskanian et al., U.S. Pat. No. 4,879,275).

Transdermal administration of an antisense PMO in accordance with the invention is described in Example 6, below, using a PMO targeted to the −3/+19 region of rat CYP3A2 (SEQ ID NO: 25). The vehicle employed was 95:5 propylene glycol/linoleic acid. Liver S-9 fractions were analyzed for analyzed for levels of PMO and for CYP3A enzyme activity, the latter by conversion of 7-benzyloxy-4-(trifluoromethyl)-coumarin (BFC) to 7-hydroxy-4-(trifluoromethyl)-coumarin (HFC). Results confirmed transdermal delivery of the oligomers and a substantial reduction in enzyme activity in animals treated with antisense to CYP3A (see Table 11, below).

EXAMPLES

The following examples are intended to illustrate but not to limit the invention.

Assay reagents were purchased from GenTest Corporation (Woburn, Massachusetts), which produces cytochrome p450 reagents and antibodies.

Example 1

Coadministration of Antisense to Rat Cytochrome p450 (CYP) 2B1 with Hexobarbital 1A. Coadministration of Antisense Olipomers, Hexobarbital and/or Inducing Agent Phenobarbital Antisense oligonucleotides were designed to be complementary to target sequences within the cytochrome p450 2B1 (rat CYP2B1) gene sequence, with the objective of improving the metabolism of hexobarbital in rats. Five phosphorothioate oligomers were synthesized according to the known rat CYP2B1 sequence (GenBank Accession No. J00719).

The antisense oligomers are shown in Table 4. The oligo 2B1-ATG (SEQ ID NO: 16) is a 22-mer having 100% complementarity to a region containing the AUG start codon on the rat CYP2B1 mRNA (SEQ ID NO: 39, shown below Table). The oligo 2B1-NRM (SEQ ID NO: 17) has 100% complementarity to the CYP2B1 mRNA starting at base 855. The oligo 2B1-BPB (SEQ ID NO: 36) has the sequence of 2B1-NRM with a two base deletion (indicated in bold in the 2B1-NRM sequence). Each of the oligos 2B1-3MM (SEQ ID NO: 37) and 2B1-CMM (SEQ ID NO: 38) has 2 bases reversed (indicated in bold) compared to the BPB sequence. These last three oligos were compared to all sequences in GenBank and did not show homology to any sequence listed in the database. The table gives the melting temperature ($T_m$), molecular weight, and % homology to CYP2B1 mRNA of each sequence.

Sequence targeted by 2B1-ATG: 3'-CCTCCTCGTTCTATGACCCGAG<u>GT</u>ACCA-5' (SEQ ID NO: 39) Sequence targeted by 2B1-NRM: 3'-TCGTTTCTTCTCTCTCTCGTCCCTCTAG-5' (SEQ ID NO: 40):

Male Sprague-Dawley rats (Sasco, Omaha) weighing between 210 to 290 grams were used for all studies. They were housed in animal quarters at the University of Nebraska Medical Center AAALAC-approved Animal Resource Facility. The animals were exposed to 12 hour light/dark cycle and fed Purina rat chow and tap water ad libitum.

Rats were injected intraperitoneally (i.p.) with the indicated ODNs (see Table 3) once per day for 2 days, in an amount of 1mg/kg body weight per injection. Control rats were injected with saline only. Rats in the "PB" groups were injected i.p. with phenobarbital (Mallinckrodt, St. Louis) at 80 mg/kg body weight per injection, once per day for 2 days. In the groups in which PB was co-administered with ODN, injections were administered simultaneously. Total volume of injections for all groups was 0.1 ml/mg body weight. Animals in the "2B1-NRM+PB+PRETREATMENT" group also received a dose of 1 mg/kg of 2B1-NRM oligomer (SEQ ID NO: 17) 24 hours prior to the first administration of 2B1-NRM plus PB.

Forty-eight hours following the first (non-pretreatment) injection of ODN and/or PB, the rats were injected i.p. with 100 mg/kg body weight hexobarbital (Sigma, St. Louis), in a total volume of 1 ml/kg body weight, prepared fresh daily. Sleep time, defined as the time period from when the rat is placed on its back to when it regains its righting reflex, was measured. Sleep times are given in Table 5 as the mean of each animal in the group ±standard deviation.

Treatment of the various groups is summarized as follows:
1. injected with saline only.
2. injected with 80 mg/kg PB per day for 2 days.
3. injected with 1 mg 2B1-NRM per day for 2 days.
4. injected simultaneously with 1 mg ODN 2B1-NRM and 80 mg/kg PB per day for 2 days.
5. same as 4 except injected with 1 mg 2B1-NRM one day before start of 2B1-NRM+PB injections.
6. injected with 1 mg ODN 2B1-ATG per day for 2 days.
7. injected simultaneously with 1 mg ODN 2B1-ATG and 80 mg/kg PB per day for 2 days.
8. injected with 1 mg ODN 2B1-BPD per day for 2 days.
9. injected with 1 mg ODN 2B1-3MM per day for 2 days.
10. injected with 1 mg ODN 2B1-CMM per day for 2 days.

TABLE 4

Characteristics of ODNs Used in Example 1

| SEQ ID NO: | Name | $T_m$ °C. | Mol. Wt. | % Identity with CYP2B1 | Sequence |
|---|---|---|---|---|---|
| 16 | 2B1-ATG | 68.0 | 6900 | 100 | 5'-GGAGCAAGATACTGGGCTCCAT-3' |
| 17 | 2B1-NRM | 50.6 | 7799 | 100 | 5'-AAAGAAGAGAGAGAGCAGGGAG-3' |
| 36 | 2B1-BPB | 47.0 | 7086 | 90 | 5'-AAAGAAGAGAGAGCAGGGAG-3' |
| 37 | 2B1-3MM | 49.8 | 7086 | 80 | 5'-AAAGAAGAGAGAGCAGGGGA-3' |
| 38 | 2B1-CMM | 49.5 | 7086 | 80 | 5'-AAAGAAGAGAAGGCAGGGAG-3' |

TABLE 5

Hexobarbital Sleep Times

| Group | SEQ ID NO: of oligomer | Sleep Time (min ± sd) | Percent of Control | Number Observed |
|---|---|---|---|---|
| 1. Control | — | 23.4 ± 4.0 | 100.0 | 10 |
| 2. Phenobarbital (PB) | — | 11.4 ± 4.5[a] | 48.7 | 5 |
| 3. 2B1-NRM | 17 | 23.0 ± 3.2 | 98.2 | 4 |
| 4. 2B1-NRM + PB | 17 | 13.5 ± 0.9 | 57.7 | 4 |
| 5. 2B1-NRM Pretreatment + PB | 17 | 13.3 ± 3.0 | 56.8 | 4 |
| 6. 2B1-ATG | 16 | 20.5 ± 5.3 | 87.6 | 4 |
| 7. 2B1-ATG + PB | 16 | 19.3 ± 4.4[b] | 82.5 | 4 |
| 8. 2B1-BPD | 36 | 8.6 ± 8.3[c] | 36.7 | 8 |
| 9. 2B1-3MM | 37 | 31.0 ± 9.6 | 132.4 | 3 |
| 10. 2B1-CMM | 38 | 23.0 ± 5.3 | 98.2 | 3 |

[a]Significantly different from control ($p < .05$).
[b]Significantly different from phenobarbital treated group ($p < .03$).
[c]Significantly different from control ($p < .001$), 2B1-3MM ($p < .001$) and 2B1-CMM ($p < .001$).

Control rats (injected only with saline during the 2-day treatment regimen) had a sleep time of about 23 minutes. PB-treated rats showed a sleep time of about 11.4 minutes, a significant reduction in sleep time over control rats, as expected. As PB stimulates CYP2B1 gene expression, hexobarbital (which is hydroxylated by CYP2B1) was more quickly metabolized in the PB-treated rat and its sedative effect was reduced.

When administered alone, oligomer 2B1-NRM, SEQ ID NO: 17 (Group 3) had no effect on sleep time compared to control, which could be attributed to a low constitutive (i.e. non-induced) level of expression of CYP2B1 in the rat.

Oligomer 2B1-NRM & PB administered together (Group 4) had no observable antisense effect. Since PB induction of gene expression is rapid (30–60 minutes) (Waxman and Azaroff, *Biochem J.* 281(3):577–92,1992), and ODN accumulation in the liver is slow (ca. 12 hours, as shown in related studies by the inventor), rats in one group were pretreated with 2B1-NRM one day before simultaneous injection of PB +2B1-NRM (Group 5). However, the resulting sleep time was essentially the same as without pretreatment.

Oligomer 2B1-ATG (SEQ ID NO: 16) alone (Group 6) did not significantly alter sleep time over control, again possibly due to low constitutive expression of CYP2B1. When 2B1-ATG and PB were injected simultaneously, however (Group 7), sleep time increased significantly over that of the PB group. Oligomer 2B1-ATG thus showed a potent-in vivo antisense effect toward PB-induced CYP2B1 expression.

Oligomer 2B1–3MM alone (SEQ ID NO: 37) slightly lengthened sleep time over the control. Oligomer 2B1-BPD (SEQ ID NO: 36) significantly reduced sleep time from control, suggesting an anomalous increase in HB metabolism. Oligomer 2B1-CMM (SEQ ID NO: 38) did not significantly alter HB sleep time from the control.

1B. Preparation of Microsomes

Microsomes were prepared, as described by Franklin and Estabrook (*Arch. Biochem. Biophys.* 143:318–29, 1971), for determination of enzyme level and activity. The rats were sacrificed using ethyl ether, and livers were perfused with 12 ml of 4% saline via the portal vein and then removed from the animal. The livers were minced, homogenized in 0.25 M sucrose (Sigma) and centrifuged at 8000×G for 20 minutes at 4° C. in a Sorvall RC2-B centrifuge (Dupont). The supernatant was saved, resuspended in 0.25 M sucrose, and centrifuged at 100,000×G for 45 minutes at 4° C. in a Sorvall OTD55B ultracentrifuge (Dupont). The pellet was resuspended in 1.15% KCl (Sigma) and centrifuged at 100,000×G for 1 hour at 4° C. The final pellet was resuspended in an equal volume buffer (10 mM Tris-acetate, 1 mM EDTA, 20% glycerol; Sigma) and frozen at −80° C.

1C. Determination of Protein Concentrations

Protein concentrations were determined by Bradford assay (M. M. Bradford, *Anal Biochem* 72:248–54, 1976). Eighty $\mu$l aliquots of homogenate, prepared as described above, were added to a 96 well plate (Becton Dickinson Labware, Lincoln Park, N.J.). Twenty $\mu$l of Bradford reagent (Bio-Rad Richmond, Calif.) was then added and the plates read at 595 nm on the microplate reader (Molecular Devices, Newport Minn.). The data was compared to standard curve generated with known concentrations of bovine serum albumin (Sigma).

1D. Determination of Enzyme Activity: PROD Assay

CYP2B1 enzyme activity was determined by pentoxyresorufin O-dealkylation (PROD) activity (Burke et al., 1985). For each microsomal sample, 1 mg protein in 1 ml 0.1 M potassium phosphate buffer, 1 ml 2 $\mu$M 5-pentoxyresorufin (Pierce, Rockford, Ill.), and 17 $\mu$l 60 mM NADPH were mixed and incubated for 10 minutes at 37° C. The mixture was then added to a 2 ml cuvette and read on a RF5000U spectrofluorophotometer (Shimadzu, Columbia, Md.), using an excitation wavelength of 530 nm and emission wavelength of 585 nm. Concentrations were calculated from a calibration curve of resorufin standards (Pierce, Rockford, Ill.). Results were recorded in nmol resorufin/mg protein/min.

Activity of microsomes from control rats was 13.8±10.1 nmol resorufin/mg prot/min. Microsomes isolated from PB groups all had significantly increased PROD activities, ranging from about 50 to 115 nmol resorufin/mg prot/min. Microsomes from 2B1-NRM, 2B1-ATG, 2B1–3MM, and 2B1-CMM treated rats (SEQ ID NOs: 17, 16, 37 and 38, respectively) showed no change from control. Although not significantly different from control, 2B1-BPD (SEQ ID NO: 36) showed a small increase in activity. (In interpreting these results, it should be noted that the pentoxyresorufin O-dealkylation (PROD) assay measures both CYP2B1 and CYP2B2.)

1E. ELISA Assay

Direct measurement of CYP2B1 protein was performed by an ELISA assay, using an antibody directed to the CYP2B1 protein (Schuurs and Van Weeman, *Clin Chim Acta* 81(1):1–40, 1977). Fifty $\mu$g of microsomal proteins per well were plated in 100 $\mu$l 0.35% sodium bicarbonate buffer overnight on a 96 well nunc-immuno plate (InterMed, Skokie, Ill.). The microsomes were washed 3× with 1% bovine serum albumin in PBS (PBS/BSA) and incubated for 1 hr at 37° C. with 200 $\mu$l PBS/BSA. The PBS/BSA was removed, and 50 $\mu$l of CYP2B1 antibody (Oxygene, Dallas) was added and incubated for 1 hour at 37° C. The microsomes were washed 5× with saline/Tween 20™ (Sigma), and 50 $\mu$l horseradish peroxidase (HRP)-conjugated secondary antibody (Bio-Rad) was added. The microsomes were incubated for 1 hour at 37° C., then washed 5× with saline/Tween 20™ and twice with 85% saline. HRP substrate (Kirkegaard & Perry Labs, Gaithersburg, Md.) (100 μl) was added, and the absorbance at 405 nm was read continuously in a microplate reader (Molecular Devices) for 1 hour. Results were recorded as HRP activity in mOD/min.

Figure 3:
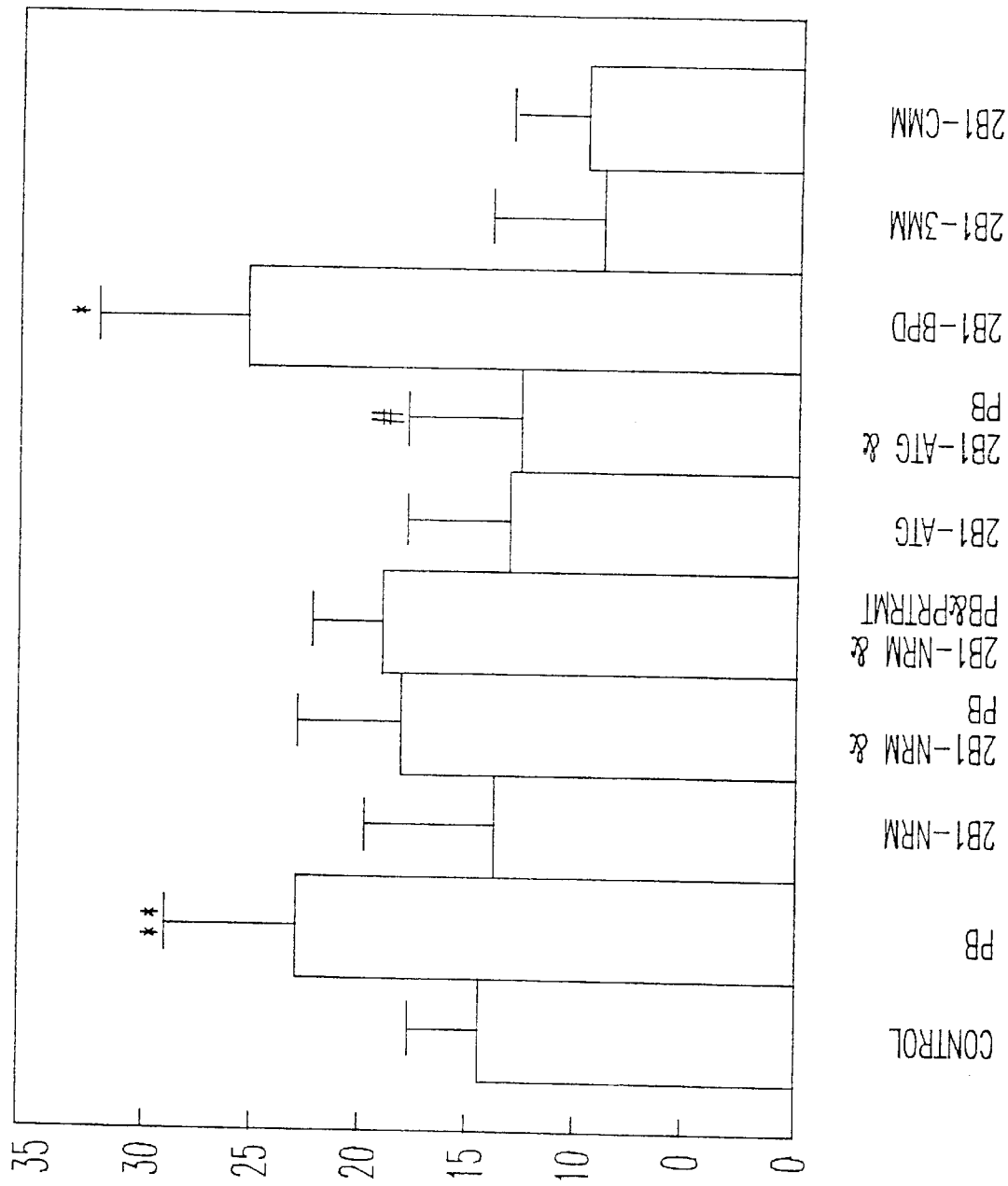
FIG. 3 depicts the results of ELISA for Cytochrome p450 2B1 (CYP2B1) from liver microsomes treated with various antisense oligonucleotides (see Example 1), in the presence or absence of the CYP2B1 inducing agent phenobarbital (PB)

The results are shown graphically in FIG. 3. The average HRP activities and n values for the various groups are given in Table 6.

TABLE 6

| Group | SEQ ID NO: of oligomer | HRP activity | n = |
|---|---|---|---|
| Control | — | 14.2 ± 3.0 | 8 |
| PB alone | — | 22.5 ± 4.2 | 5 |
| 2B1-NRM | 17 | 13.8 ± 5.6 | 4 |
| 2B1-NRM + PB | 17 | 17.9 ± 4.6 | 4 |
| 2B1-NRM + PB/Pretreatment | 17 | 18.7 ± 0.3 | 4 |
| 2B1-ATG | 16 | 13.2 ± 4.4 | 4 |
| 2B1-ATG + PB | 16 | 12.9 ± 5.0 | 5 |
| 2B1-BPD | 36 | 25.1 ± 6.6 | 3 |
| 2B1-3MM | 37 | 9.2 ± 5.0 | 3 |
| 2B1-CMM | 38 | 10.1 ± 3.3 | 3 |

As expected, HRP activity of microsomes treated with PB alone was significantly greater than the activity of microsomes from control rats, due to induction of expression of the CYP2B1 gene by PB. Microsomes of rats treated with oligomers 2B1-NRM, 2B1-ATG, 2B1-3MM, and 2B1-CMM (SEQ ID NOs: 17, 16, 37 and 38, respectively) showed no change in HRP activity over control microsomes.

Microsomes from rats in the 2B1-NRM+PB group and the 2B1-NRM+PB+PRETREATMENT group showed a decrease in HRP activity over that of the PB-alone treatment group, indicating an inhibitory effect of the 2B1-NRM oligomer on the amount of PB-induced CYP2B1 present in the microsomal fractions.

Microsomes from rats in the 2B1-ATG+PB treatment group showed a significant decrease in HRP activity over the PB-alone group, indicating that the 2B1-ATG oligomer had a significant inhibitory effect on PB-induced production of CYP2B1, in agreement with the significant sleep time increases observed in that rat treatment group. Microsomes from 2B1-BPD treated rats showed an increase in CYP2B1 over control in the ELISA assay, which concurs with the anomalous sleep time reduction observed in 2B1-BPD treated rats.

1F. Determination of CYP2E1 Induction

Microsomal PNP (p-nitrophenol hydroxylase) activity was used as a measure of induction of CYP2E1, as PB is known to induce many different CYPs, including CYP2E1. CYP2E1 activity was determined by PNP activity as described in Reinke and Moyer, Drug Metab. Dispos. 13:548–52, 1985; Koop, Mol. Pharmacol. 29:399404, 1986). Activity was recorded as optical density (OD) per milligram of protein per minute.

Microsomes from control rats had a PNP activity of 0.49±0.05 OD/mg prot/min. Microsomes isolated from rat groups treated with PB (PB; 2B1-NRM+PB; 2B1-NRM+PB+pretreatment; 2B1-ATG & PB) all showed significant increases in PNP activities over that of control, demonstrating induction of CYP2E1 by PB. Since each PB group showed approximately equivalent PNP activities, the ODNs did not appear to interfere with the PB induction mechanism of CYP2E1. Microsomes isolated from rats treated with oligomers 2B1-NRM, 2B1-ATG, 2B1-BPD, 2B1-3MM and 2B1-CMM (SEQ ID NOs: 17, 16, 36, 37 and 38, respectively) alone (no PB) showed no significant differences in PNP activities from control values.

All data was reported as mean±standard deviation. The mean and standard deviation were determined by the computer program InStat2 (GraphPad, San Diego). The p values were also calculated by InStat2 using the Tukey-Kramer Multiple Comparisons Test.

Example 2

Antisense Inhibition of Rat Cytochrome p450 (CYP) 2E1

Substrates to cytochrome p450 isozymes frequently control the rate of their own metabolism by modulating isozyme gene expression (Eliasson et al., J Biol Chem. 267(22): 15765–9, 1992). Cytochrome p450 IIE1 (CYP2E1) up-regulation has been attributed to increased transcription, mRNA stabilization and enhanced stability of the protein. CYP2E1 gene expression is induced by low molecular weight compounds such as ethanol, acetone, and pyrazole.

The exemplary rat CYP2E1 antisense sequences given in Table 2 were used to evaluate the effectiveness of antisense targeting of specific sequences important to the processes of pre-mRNA splicing and mRNA translation.

Oligonucleotides: Phosphorothioate oligonucleotides were synthesized on a 1 μmole scale by use of an Applied Biosystem Model 380A DNA Synthesizer (Foster City, Calif. and University of Nebraska DNA synthesis core facility), according to standard methodology (e.g. G. Zon and W. J. Stec, in Eckstein, F. (ed.), OLIGONUCLEOTIDES AND ANALOGUES: A PRACTICAL APPROACH (IRL Press at Oxford University Press), pp. 87–108 (1991). The oligonucleotides had sequences antisense to rat cytochrome CYP2E1 mRNA and pre-mRNA sequences (Umeno et al., Biochemistry 27(25):9006–13, 1988); GenBank Locus RATCYP45I, Accession M20131).

The anti-2E1 30-mer, 5'-(GGT TTA TTA TTA GCT GCA GTT GGC TAT CAT)-3' (SEQ ID NO: 18), is antisense to a region in the rat CYP2E1 sequence beginning at position 1406 and containing a sequence upstream of the ATG translation start site. The sequences of the anti-2E1 20-mers are as follows: 5'-(CCA AGA ACC GCC ATG GTG CC)-3' (SEQ ID NO: 19), antisense to a region beginning at position 1560 and targeting the ATG translation start site; 5'-(ACC TTG GTG AAA GAC TTG GG)-3' (SEQ ID NO: 20) antisense to a region beginning at position 1725 and targeting the splice donor of exon 1; 5'-(CCT TGT TCT TGT ACT CCT GG)-3' (SEQ ID NO: 21) antisense to a region beginning at position 2645 and targeting the splice donor of exon 2; 5'-(GAG AAG CAT GGT CAC CTG GA)-3' (SEQ ID NO: 22) antisense to a region beginning at position 6681 and targeting the splice donor of exon 4; and 5'-(CCA ACA CAC ACA CGC TT TCC)-3' (SEQ ID NO: 23), antisense to a region beginning at position 11591 and targeting the splice acceptor of exon 9. Two nonsense oligonucleotides prepared for control purposes include the 27-mer 5'-(TCG TCG GTC TCT CCG CTT CTT CCT GCC)-3' (SEQ ID NO: 41), antisense to rev of HIV-1 (Matsukura et al., *Proc Natl Acad Sci USA* 86(11):4244–8, 1989) and the 20-mer 5'-(TCG TGA TGA ATT CTG TCG AG)-3' (SEQ ID NO: 42), with no homologous complementary sequence in the rat genome.

Cell Transfection: The rat hepatoma cell line, H42E, was purchased from American Type Culture Collection (Bethesda, Md.). The cells were maintained in RPMI-1640 media (Sigma, St. Louis, Mo.), supplemented with 10% heat inactivated fetal bovine serum (Gibco, Grand Island, N.Y.), penicillin G (10,000 units/ml) and streptomycin (10% mg/ml)(Sigma). The cells were subcultured at 3–4 day intervals at a density of $2 \times 10^5$ cells per 25 cm$^2$ flask in 5 ml of medium, and incubated at 37° C. in a humidified atmosphere of 95% air, 5% $CO_2$.

The H42E cells were plated ($2 \times 10^6$ to $1.25 \times 10^5$ for the 1 to 5 day timepoints) in 10 ml RPMI+10% FBS in 100 mm tissue culture dishes (Becton Dickenson, Oxnard, Calif.) and allowed to adhere overnight. Antisense oligonucleotide (3.0 μM) and pyrazole (16 μM; Sigma) were added, and dishes were incubated at 37° C. for 1 to 5 days. Cells were harvested in 2 ml 0.1 M $K_2HPO_4$ pH 7.2 and homogenized into microsomes.

Eight antisense oligonucleotides, as described above, were employed to test the ability of the various mRNA target regions to inhibit pyrazole-induced synthesis of the CYP2E1 enzyme. Six antisense oligonucleotides, as described above (SEQ ID NOs: 18–23), were specific to different regions along CYP2E1 mRNA. The last two sequences, MM3 and BUD (SEQ ID NOs: 41 and 42, respectively), were nonsense oligonucleotides with no targets within the CYP2E1 gene.

The relative concentrations of CYP2E1 enzyme in prepared microsomes were measured by use of ELISA. Microsome dilutions of 50 to 6.25 μg/ml of each sample were plated in coupling buffer (0.06% sodium carbonate, 0.29% sodium bicarbonate, pH 9.6) in 96 well immunoassay NUNC plates (VWR Scientific, Chicago, Ill.). Plates were incubated overnight at 4° C. to allow protein to adhere to wells. Wells were washed 10× with 0.05% Tween 20™ (Aldrich, Milwaukee, Wis.)/PBS, the last wash with PBS only, then blocked for 2 hours with 3% BSA (Sigma)/PBS. Wells were washed as before. The primary antibody, anti-Cytochrome p450 2E1 (Oxygene, Dallas, Tex.), diluted 1:200 in 1% BSA/PBS, was added and plates were incubated for 1.5 hours. Wells were washed, and a 1:2000 dilution of the secondary antibody, horseradish peroxidase (HRP) conjugate (Bio-Rad, Richmond, Calif.), was added. Plates were incubated 2 hours and washed. A 1:1 dilution of ABTS Peroxidase Substrate and Peroxidase Solution B (Kirkegaard and Perry, Gaithersburg, Md.) were added to the wells. Plates were read kinetically at 405 nm every 30 seconds for 1 hour with an OD max of 0.500 (Pruslin, *J Immunol Methods* 137(1):27–35, 1991).

Results are given in Table 7.

TABLE 7

Characteristics of antisense CYP2E1 oligomers and effect on CYP2E1 enzyme levels

| SEQ ID NO: | TARGET | SITE | $T_m$ | G/C | ELISA (% of control) |
|---|---|---|---|---|---|
| 18 | upstream ATG start | 1406 | 58.7° C. | 36.7% | 75.8 ± 11.3[a] |
| 19 | ATG start site | 1560 | 61.9° C. | 65.0% | 51.7 ± 12.0[a] |
| 20 | exon 1 splice donor | 1725 | 50.6° C. | 50.0% | 66.3 ± 9.7a |
| 21 | exon 2 splice donor | 2645 | 46.2° C. | 50.0% | 89.3 ± 6.9 |
| 22 | exon 4 splice donor | 6681 | 52.2° C. | 55.0% | 92.0 ± 7.6 |
| 23 | exon 9 splice accpt | 11591 | 53.7° C. | 55.0% | 62.9 ± 7.4[a] |
| 41 | nonsense control | MM3 | 70.3° C. | 63.0% | 99.7 ± 8.7 |
| 42 | nonsense control | BUD | 48.1° C. | 45.0% | 95.1 ± 9.0 |

[a]$p < 0.05$.

Several of the oligonucleotides produced significant reduction in levels of CYP2E1 enzyme. The antisense oligomers 2E1–1560, 2E1–11591, 2E1–1725 and 2E1–1406 (SEQ ID NOs: 19, 23, 20, and 18, respectively) reduced enzyme levels to 52%, 63%, 66% and 76% of control, pectively. Treatment with the other CYP2E1 specific oligonucleotides, as well as the nonsense oligonucleotides, resulted in CYP2E1 levels that were not significantly different from the control level.

Figure 4:
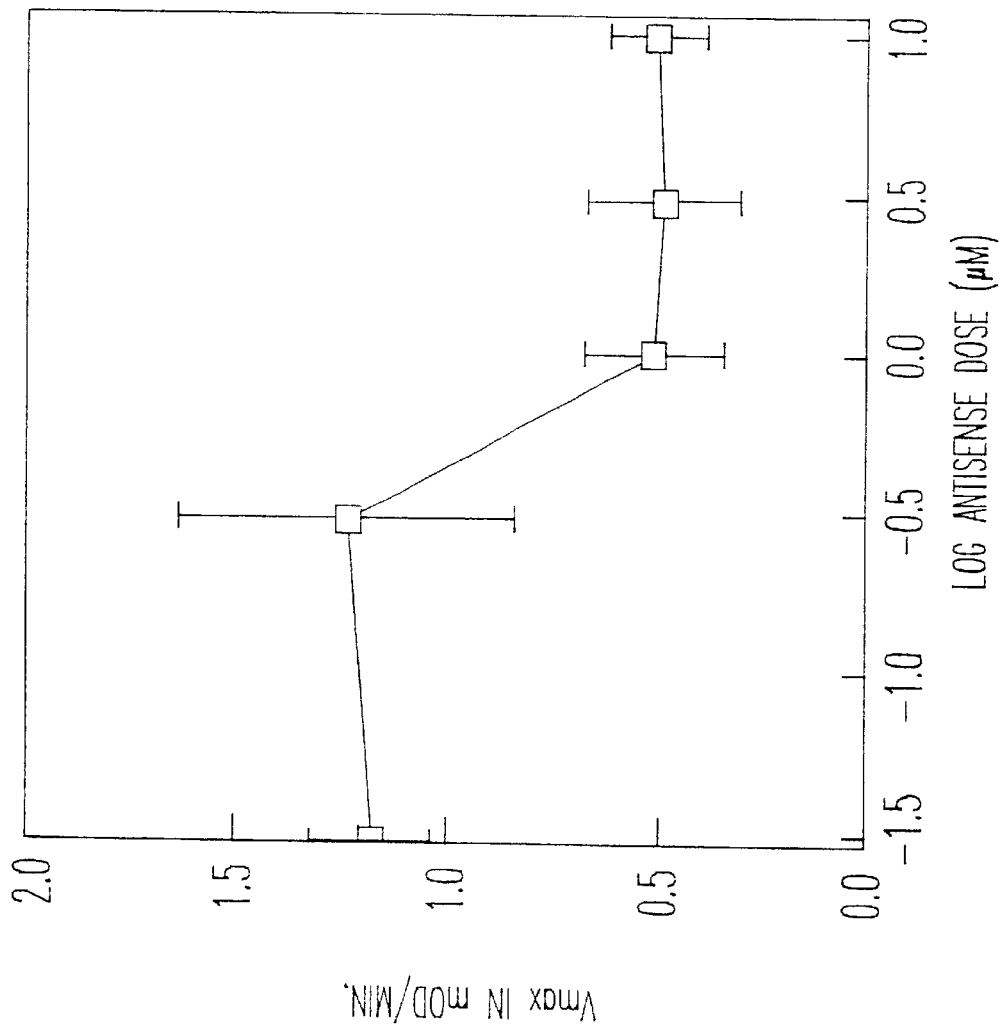
FIG. 4 depicts the levels of CYP2E1 isozyme from cultures treated with increasing amounts of the antisense oligonucleotide 2E1-1560 (SEQ ID NO: 19), assayed by ELISA for comparative amounts of the CYP2E1 isozyme present (see Example 2)
Figure 5A:
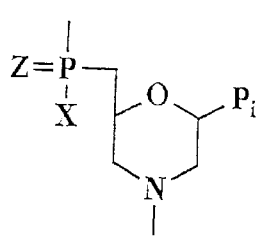
FIGS. 5A–5E shows several preferred subunits having 5-atom (A), six-atom (B) and seven-atom (C–E) linking groups suitable for forming polymers.
Figure 5B:
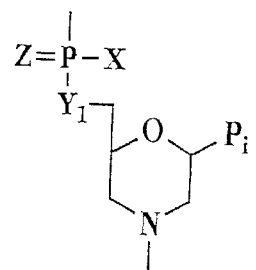
Figure 5C:
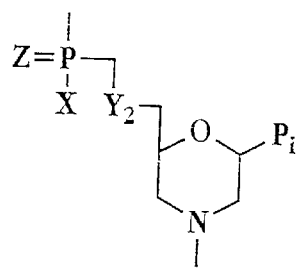
Figure 5D:
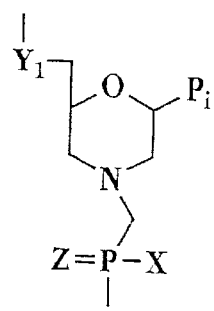
Figure 5E:
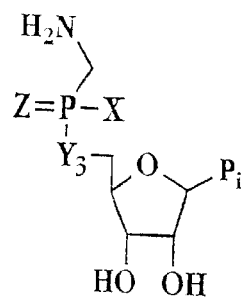

Varying doses of the antisense oligonucleotide 2E1–1560 (SEQ ID NO: 19) were investigated for inhibition of the CYP2E1 enzyme in H42E cultures. The cultures showed an increase in inhibition on an increase in oligo concentration from 0.3 μM to 3 μM, at which the enzyme level was approximately 41% of control. Above this level, the CYP2E1 protein inhibition leveled off, showing little additional inhibition at 10 μM of oligonucleotide (FIG. 4).

Example 3

Antisense Inhibition of Rat Cytochrome p450 (CYP) 3A2 by PS and PMO Oligonucleotides and Effect on Midazolam Efficacy Antisense oligonucleotides complementary to target sequences within the cytochrome p450 3A2 (rat CYP3A2) gene sequence were prepared, with the objective of increasing the effectiveness of midazolam (MZ) in rats. Two phosphorothioate (PS) and two PMO oligomers were synthesized according to the known rat CYP3A2 sequence (GenBank Accession No. U09742; see Table 2).

TABLE 8

Antisense Rat CYP3A2 Oligonucleotide Sequences and Controls
Rat CYP3A2 mRNA (Accession #U09742):

```
        -8        -1      10        20
5'-AAGCAGGG AUG GACCUGC UUUCAGCUCU CACACUGG-3'
              (SEQ ID NO: 45)
```

| SEQ ID NO: | Name | Sequence | Type |
|---|---|---|---|
| 24 | ATG3A2/PS | 5'-TGAGAGCTGAAAGCAGGTC<u>CAT</u>-3' | PS DNA |
|  | AUG3A2/PMO | 5'-UGAGAGCUGAAAGCAGGUC<u>CAU</u>-3' | PMO RNA |
| 25 | (-3)ATG3A2/PMO-C5M | 5'-GAGMTGAAAGMAGGTM<u>MATMMM</u>-3 | PMO RNA/C-5 |
| 43 | REV3A2/PS | 5'-TACCTCGACGAAAGTCGAGAGT-3' | PS DNA; reverse control |
|  | REV3A2/PMO | 5'-UACCUCGACGAAAGUCGAGAGU-3' | PMO RNA; reverse control |
| 44 | ATGMYC/PS | 5'-ACGTTGAGGGGCAUCGTCC-3' | PS DNA; myc control |
|  | AUGMYC/PMO | 5'-ACGUUGAGGGGCAUCGUCC-3' | PMO RNA; myc control |

M5'-methyl cytidine

The antisense oligomers are shown in Table 8. The oligos designated AUG3A2/PMO and ATG3A2/PS have the sequence designated SEQ ID NO: 24, which targets the ATG start codon. In (-3)ATG3A2/PMO-C5M (SEQ ID NO: 25, a three-base shift from SEQ ID NO: 24), several cytidine bases are 5'-methylated, as shown in the Table. Reverse-sequence oligos (SEQ ID NO: 43) and a c-myc sequence (SEQ ID NO: 44) were used as controls.

Male Sprague-Dawley rats (Sasco, Omaha) weighing between 210 to 290 grams were used for all studies. The animals were exposed to 12 hour light/dark cycle and fed Purina rat chow and tap water ad libitum.

A dose-response curve for MZ was determined by injecting rats i.p. with 20, 50 or 70 mg/kg of MZ and recording sleep times (data not shown). Sleep time was defined as the time period from when the rat was placed on its back to when it regained its righting reflex.

Sleep time was measured after i.p. injection of 50 mg/kg MZ (Hoffman-La Roche, Nutley, N.J.) at 0 (day 1), 24 (day 2) and 48 h (day 4). The volume of the injection was from 2.0 to 2.4 ml/rat. All animals demonstrated loss of righting reflex within 2 min after i.p. injection of MZ. The rats were treated with 0.25, 0.50 or 1.00 mg antisense ODN i.p. immediately after the animal had regained its righting reflex determined at 0 and 24 h. Control rats received saline only. Total volume injection was 0.1 ml in saline.

Preparation of Microsomes

Microsomes were prepared, as described by Franklin and Estabrook (cited above) for determination of enzyme level and activity. The rats were sacrificed using ethyl ether, and livers were perfused with 12 ml of 4% saline via the portal vein and then removed from the animal. The livers were minced, homogenized in 0.25 M sucrose (Sigma) and centrifuged at 8000×G for 20 minutes at 4° C. in a Sorvall RC2-B centrifuge (Dupont). The supernatant was saved, resuspended in 0.25 M sucrose, and centrifuged at 100,000×G for 45 minutes at 4° C. in a Sorvall OTD55B ultracentrifuge (Dupont). The pellet was resuspended in 1.15% KCl (Sigma) and centrifuged at 100,000×G for 1 hour at 4° C. The final pellet was resuspended in an equal volume buffer (10 mM Tris-acetate, 1 mM EDTA, 20% glycerol; Sigma) and frozen at −80° C.

Determination of Protein Concentrations

Protein concentrations were determined by Bradford assay (M. M. Bradford, *Anal Biochem* 72:248–54, 1976). Eighty pl aliquots of homogenate, prepared as described above, were added to a 96 well plate (Becton Dickinson Labware, Lincoln Park, N.J.). Twenty μl of Bradford reagent (Bio-Rad Richmond, Calif.) was then added and the plates read at 595 nm on the microplate reader (Molecular Devices, Newport, Minn.). The data was compared to standard curve generated with known concentrations of bovine serum albumin (Sigma).

Liver Microsomal Assays for CYP3A2

Erythromycin demethylation (ED) was used a measure of CYP3A2 enzymatic activity (Gonzalez, *Pharmacol. Rev.* 40:243–87, 1989). Activity was recorded as micromoles of formaldehyde per milligram of protein per minute.

Western Blot of CYP3A2

Western blot analysis of CYP3A2 was carried out using the method described by Tracewell et al., *Toxicol Appl Phanmacol.* 135(2):179–84, 1995. Band intensities were determined by a Molecular Dynamics Personal Densitometer (Sunnyvale, Calif.) with ImageQuant version 3.3 software (Molecular Dynamics).

Statistical Analysis

All microsomal data were reported as mean standard error of the mean (S.E.) as determined by the computer program InStat2 (GraphPad, San Diego). The P values were also calculated by InStat2 with the Tukey multiple comparison test. Standard curve and graphs were generated using Prism (GraphPad).

Results:

Sleep Time: Table 9 shows the change in sleep time (MZ ST) and ED activity (a marker for CYP3A2) for animals receiving the various treatments. Both the PMO and PS oligos targeting the start codon (SEQ ID NOs: 24 and 25) showed an increase in sleep time, as would result from inhibition of CYP3A2 and consequent inhibition of metabolism of the MZ. The PMO oligo, however, was effective at one-tenth the concentration of the PS oligo. Control oligos (SEQ ID NOs: 43 and 44) showed little or no change from the saline-only control.

ED Activity: All of the anti-3A2 oligos (SEQ ID NOs: 24 and 25) reduced ED activity to some extent, with the 5'-C-methyl modified PMO (SEQ ID NO: 25) showing greater activity than the unmodified oligo. Activity in animals administered control oligos was not significantly different from the saline control.

TABLE 9

Effect of Anti-CYP3A2 Oligonucleotides on MZ Sleep Time and ED Activity in Rats

| Treatment (no. of animals) | SEQ ID NO: | Dose (µg/day) | MZ ST | ED |
|---|---|---|---|---|
| Saline control (10) | — | — | 22.3 ± 0.9 | 100 ± 3.3 |
| ATG3A2/PS | 24 | 1000 | 35.3 ± IS | 52 ± 13[a] |
| AUG3A2/PMO (4) | 24 | 100 | 33.3 ± 2.3[a] | 80 ± 5[b] |
| (−3)ATG3A2/PMO-C5M (4) | 25 | 100 | nd | 55 |
| REV3A2/PS (3) | 43 | 1000 | 22.4 ± 0.6 | 91 |
| REV3A2/PMO (3) | 43 | 100 | 20.3 ± 1.3 | 99 |
| ATGMYC/PS (4) | 44 | 1000 | 22.8 ± 1.3 | 113 |
| AUGM:YC/PMO (3) | 44 | 100 | 20.6 ± 0.6 | 110 |

All values represent the mean ± standard error of the mean. MZ ST - midazolam sleep time, min; Ed - erythromycin demethylase activity (in vitro marker for CYP3A2), µmol HCOH/mg/min.
[a]Significantly different from saline myc, and rev groups, p < 0.01.
[b]significantly different from myc and saline groups, p < 0.05.

Example 4

Antisense Inhibition of Human CYP3A4 in Transfected Cells

V79 cells were stably transfected with the human CYP3A4 gene. The cells were scrape loaded with 10 µM PMO having the sequences shown below, targeting the ATG start codon of human CYP3A4 mRNA (SEQ ID NOs: 46, 47, and 35; see Table 2). A sequence targeting the ATG rat CYP3A2 (SEQ ID NO: 25, with C-methyl substitution) was also employed. Activity was assayed in S-9 fractions via 7-benzyloxy-4-(trifluoromethyl)-coumarin conversion to fluorescent product 7-hydroxy-4-(trifluoromethyl)-coumarin, a CYP3A4 specific reaction.

TABLE 10

Antisense Inhibition of Human CYP3A4

| | | |
|---|---|---|
| 5'-CTG GGA TGA GAG CCA TCA C-3' | SEQ ID NO: 46 | human CYP3A4 |
| 5'-CTG GGA TGA GAG CCA TCA CT-3' | SEQ ID NO: 47 | " |
| 5'-GT CTG GGA TGA GAG CCA TCA-3' | SEQ ID NO: 35 | " |
| 5'-GAG MTG AAA GMA GGT MMA TMM M-3' | SEQ ID NO: 25 | rat CYP3A2 |

| Treatment | pmoles/50 µg protein in 10 minutes |
|---|---|
| Vehicle (control) | 23.80 |
| Scrambled control oligo | 21.60 |
| SEQ ID NO: 25 | 21.90 |
| SEQ ID NO: 46 | 13.10 |
| SEQ ID NO: 47 | 13.40 |
| SEQ ID NO: 35 | 16.50 |

As shown in the table, the human antisense sequences significantly reduced enzyme activity. The anti-rat oligo, which in this case has only about 55% homology with the human sequence targeted, showed no reduction in enzyme activity.

Example 5

Effectiveness of Orally Administered PMO Antisense Oligomers

FIG. 7 shows a Western blot of liver microsome samples obtained from rats which were administered a phosphorodiamidate morpholino oligonucleotide (PMO) antisense to the rat CYP3A2 gene (SEQ ID NO: 25, with no C-methyl modifications), either i.p. or orally. The blot was first probed with anti-rat CYP3A2 antibodies. After stripping off antibodies, the blot was re-probed with antibodies to NADPH Reductase as a control for total protein loading in the various lanes.

Each rat weighed approximately 200 gm, and was treated 24 hours prior to organ harvesting with the following: saline, injected intraperitoneally (lane 1); 15 nmoles of PMO 1-0-328, injected intraperitoneally (lanes 2 and 3); 60 nmoles of PMO 1-0-328, administered orally (lanes 4 and 5). Each lane corresponds to a different test animal.

No significant reduction in CYP3A2 protein compared to the saline-injected control was observed 24 hours after i.p. injection of 15 nmoles (approx. 0.5 mg/kg body weight) PMO (lanes 2–3); however, in other experiments, a modest decrease in CYP3A2 enzyme activity was observed under these conditions. Furthermore, a significant reduction in CYP3A2 protein level was observed by Westemf blot when a second injection of 15 nmoles PMO was administered 24 hours following the first, and organs were harvested 24 hours thereafter (data not shown).

In a test of the oral bioavailability of antisense PMOs, 60 nmoles of the antisense PMO (2 mg/kg body weight, four times the i.p dose used above) were administered to rats by oral gavage, and organs were harvested 24 hours later. Lanes 4 and 5 show a significant reduction in CYP3A2 protein compared to lanes 2 and 3, showing that the relative oral bioavailability of the antisense PMO is substantially greater than 25% of the i.p. administered PMO.

Example 6

Effectiveness of Transdermally Administered PMO Antisense Oligomers

A PMO targeted to the −3/+19 region of rat CYP3A2, having SEQ ID NO: 25 (5'-GAG CTG AAA GCA GGT CCA TCC C-3'), was used. Three groups of 4 animals each were treated as follows:

| Antisense Group: | 3 mg/rat AVI-4472 | (SEQ ID NO: 25) |
| Control Group: | 3 mg/rat AVI-4126 | (antisense to c-myc; SEQ ID NO: 44) |
| Vehicle Group: | Vehicle only | |

For the Antisense and Control groups, a formulation of 3 mg PMO in 100 µl of 95:5 propylene glycol/linoleic acid (vehicle) was applied over the right rear flank of 280–300 gm rats. The area was shaved immediately prior to PMO administration and was determined to be free of any visible cuts or bruises. The PMO formulation was applied over an area of 200 $mm^2$ using a plastic ring as guide. It was observed that the formulation disappeared visually from the skin in 3 to 5 minutes.

All rats were euthanized 24 hrs following the transdermal application. Liver S-9 fractions were analyzed for CYP3A enzyme activity by conversion of 7-benzyloxy-4-(trifluoromethyl)-coumarin (BFC) to 7-hydroxy4-(trifluoromethyl)-coumarin (HFC). The reaction is specific for CYP3A, and the fluorescent product formation can be monitored at an excitation wavelength of 409 nm and emission wavelength of 530 nm.

Liver samples from the Control PMO group were analyzed for levels of PMO, and revealed 9.9±0.7 µg PMO/ rat liver 24 hrs following transdermal application, establishing transdermal delivery of the oligomers. As the data in Table 11 shows, a substantial reduction in enzyme activity was observed in the animals treated with antisense to CYP3A, while the results for the control antisense were essentially similar to the vehicle-only control.

TABLE 11

Reduction of CYP3A2 Activity by Transdermally Delivered Antisense PMO

| | BFC Activity Fluorescence (a.u.), 100 µg S-9/30 min. | | | | | |
|---|---|---|---|---|---|---|
| Route | 1 | 2 | 3 | 4 | AVG | STD. |
| Saline I.P. | 580.0 | 604.0 | 511.0 | 564.0 | 564.8 | 39.4 |
| 4126 transdermal | 619.0 | 502.0 | 557.0 | 542.0 | 555.0 | 48.6 |
| 4472 Transdermal | 313.0 | 402.0 | 441.0 | 301.0 | 364.3 | 68.2 |

While the invention has been described with reference to specific methods and embodiments, it will be appreciated that various modifications may be made without departing from the invention.

It is claimed:

1. A method of inhibiting metabolism of a drug administered to a subject, comprising co-administering with said drug a morpholino antisense oligomer effective to reduce expression of a cytochrome p450 enzyme that catalyzes metabolism of the drug in said subject, by hybridizing to a target RNA molecule which encodes said enzyme, wherein the cytochrome p450 enzyme is selected from the group consisting of CYP2B1, CYP2E1, CYP3A2, and CYP3A4, and wherein said morpholino antisense oligomer has a base sequence selected from the group consisting of: SEQ ID NO: 16, for inhibition of CYP2B1; SEQ ID NOs: 18–20 and 23, for inhibition of CYP2E1; SEQ ID NOs: 24 and 25, for inhibition of CYP3A2; and SEQ ID NOs: 35, 46, and 47, for inhibition of CYP3A4; and is administered transdermally to the subject.

2. The method of claim 1, wherein the drug either induces said drug-metabolizing cytochrome p450 enzyme, or is administered to a subject who has been exposed to a xenobiotic agent which induces such an enzyme.

3. The method of claim 2, wherein said dnig induces at least one cytochrome p450.

4. The method of claim 2, wherein said xenobiotic agent induces at least one cytochrome p450.

5. The method of claim 1, wherein the antisense oligomer is at least 15 nucleotides in length.

6. The method of claim 1, wherein the antisense oligomer has an uncharged backbone comprising phosphoramidate or phosphorodiamidate linkages.

7. The method of claim 1, wherein the antisense oligomer hybridizes to a region of said target RNA with a $T_m$ greater than 37° C.

8. The method of claim 1, wherein said cytochrome p450 is CYP3A4.

9. The method of claim 8, wherein said subject is a human subject.

10. The method of claim 3, wherein said cytochrome p450 is from the CYP3A subfamily, and said drug is phenobarbital or hexobarbital.

11. The method of claim 3, wherein said cytochrome p450 is CYP3A4, and said drug is an antibiotic selected from the group consisting of clarithromycin, erythromycin, rifampicin, rifampin, rifabutin, and rapamycin.

12. The method of claim 3, wherein said cytochrome p450 is CYP3A4, and said drug contains an estrogen or estradiol.

13. The method of claim 4, wherein said cytochrome p450 is CYP3A4, said drug is a protease inhibitor or non-nucleoside reverse transcriptase inhibitor, and said xenobiotic is a CYP3A4-inducing non-nucleoside reverse transcriptase inhibitor.

14. The method of claim 1, wherein said oligomer has the sequence presented herein as SEQ ID NO: 47.

15. The method of claim 8, wherein said drug is paclitaxel.

* * * * *

SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 1:

GGAGCAAGAT ACTGGGCTCC AT     22

(2) INFORMATION FOR SEQ ID NO: 2:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 2:

AAAGAAGAGA GAGAGCAGGG AG                                             22

(2) INFORMATION FOR SEQ ID NO: 3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 3:

AAAGAAGAGA GAGCAGGGAG                                                20

(2) INFORMATION FOR SEQ ID NO: 4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 4:

AAAGAAGAGA GAGCAGGGGA                                                20

(2) INFORMATION FOR SEQ ID NO: 5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 5:

AAAGAAGAGA AGGCAGGGAG                                                20

(2) INFORMATION FOR SEQ ID NO: 6:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: mRNA (iii) HYPOTHETICAL: NO (iv) ANTI-SENSE: NO (xi) SEQUENCE DESCRIPTION: SEQ ID NO: 6:

CCTCCTCGTT CTATGACCCG AGGTACCA                                               28

(2) INFORMATION FOR SEQ ID NO: 7:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: mRNA (iii) HYPOTHETICAL: NO (iv) ANTI-SENSE: NO (xi) SEQUENCE DESCRIPTION: SEQ ID NO: 7:

TCGTTTCTTC TCTCTCTCGT CCCTCTAG                                               28

(2) INFORMATION FOR SEQ ID NO: 8:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 8:

GGTTTATTAT TAGCTGCAGT TGGCTATCAT                                             30

(2) INFORMATION FOR SEQ ID NO: 9:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 9:

CCAAGAACCG CCATGGTGCC                                                        20

(2) INFORMATION FOR SEQ ID NO: 10:

(i) SEQUENCE CHARACTERISTICS:
            (A) LENGTH: 20 base pairs
            (B) TYPE: nucleic acid (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 10:

ACCTTGGTGA AAGACTTGGG                                            20

(2) INFORMATION FOR SEQ ID NO: 11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 11:

CCTTGTTCTT GTACTCCTGG                                            20

(2) INFORMATION FOR SEQ ID NO: 12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 12:

GAGAAGCATG GTCACCTGGA                                            20

(2) INFORMATION FOR SEQ ID NO: 13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 13:

CCAACACACA CACGCTTTCC                                            20

(2) INFORMATION FOR SEQ ID NO: 14:

(i) SEQUENCE CHARACTERISTICS:
        (A) LENGTH: 27 base pairs
        (B) TYPE: nucleic acid
        (C) STRANDEDNESS: single
        (D) TOPOLOGY: linear

```
            (ii) MOLECULE TYPE: cDNA (iii) HYPOTHETICAL: NO (iv) ANTI-SENSE: YES (xi) SEQUENCE DESCRIPTION: SEQ ID NO: 14:

TCGTCGGTCT CTCCGCTTCT TCCTGCC                                          27

(2) INFORMATION FOR SEQ ID NO: 15:

(i) SEQUENCE CHARACTERISTICS:
                  (A) LENGTH: 20 base pairs
                  (B) TYPE: nucleic acid
                  (C) STRANDEDNESS: single
                  (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 15:

TCGTGATGAA TTCTGTCGAG                                                  20
```